United States Patent [19]

Burke, Jr. et al.

[11] Patent Number: 5,688,992
[45] Date of Patent: Nov. 18, 1997

[54] O-MALONYLTRYROSYL COMPOUNDS, O-MALONYLTRYROSYL COMPOUND-CONTAINING PEPTIDES, AND USE THEREOF

[75] Inventors: Terrence R. Burke, Jr., Bethesda; Bin Ye, Gaithersburg; Miki Akamatsu, Rockville; Hemanta K. Kole, Baltimore; Xinjian Yan; Peter R. Roller, both of Rockville, all of Md.

[73] Assignee: The United States of America as represented by the Department of Health and Human Services, Washington, D.C.

[21] Appl. No.: 414,520

[22] Filed: Mar. 31, 1995

[51] Int. Cl.$^6$ .................. C07C 57/145; A61K 31/19; A61K 31/195; A61K 38/00
[52] U.S. Cl. .................. 560/82; 560/76; 562/65; 514/561; 514/563; 514/570; 514/2
[58] Field of Search .................. 514/14, 561, 563; 562/565; 560/82

[56] References Cited

U.S. PATENT DOCUMENTS 5,200,546  4/1993  Burke, Jr. et al. .................. 558/190

OTHER PUBLICATIONS

Hunter, T. Protein–Tyrosine Phosphatases: Theother side of the coin. Cell, 58:1013–1016, Sep. 1989.

Burke, Jr., T.R., et al. (1991) Preparation of 4-[bis(tert-butyl)phosphonomethyl]-N-Fmoc-DL-phenyalanine; a Hydrolytically Stable Analog of O-Phosphotyrosine Potentially Suitable for Peptide Synthesis, Synthesis 11:1019–1020.

Burke, Jr., T.R., et al. (1993) Synthesis of 4-Phosphono(Difluoromethly)-D-L-Phenylalanine and N-Boc and N-Fmoc Derivatives Suitable Protected for Solid-Phase Synthesis of Nonhydrolyzable Phosphotyrosyl Peptide Analogues, Tetrahedron Letters 34:4125–4128.

Burke, Jr., T.R., et al. (1993) Preparation of Fluoro– and Hydroxy-4-Phosphonomethyl-D,L-Phenylalanine Suitably Protected for Solid-Phase Synthesis of Peptides containing Hydrolytically Stable Analogues of O-Phosphotyrosine, J. Organ Chem. 58:1336–1340.

Burke, Jr., T.R., et al. (1994) Nonhydrolyzable Phosphotryosyl Mimetics for the Preparation of Phosphotase-Resistant SH2 Domain Inhibitos, Biochemistry 33:6490–6494.

Burke, Jr., T.R., et al. (1994) Cyclic Peptide Inhibitors of Phosphatidylinositol 3–Kinase p85 SH2 Domain Binding, Biochem. Biophys. Res. Commun. 201:1148–1153.

Burke, Jr., T.R., et al. (1994) Potent Inhibition of Insulin Receptor Dephosphorylation by a Hexamer Peptide Containing the Phosphotyrosyl Mimetic F2Pmp, Biochem. Biophys. Res. Commun. 204:129–134.

Burke, Jr., T.R., et al. (1995) Non Phosphorus Containing Phosphotyrosyl Mimetics Amenable to Prodrug Derivatization and Their use in Solid-Phase Peptide Synthesis of SH2 Domain and phosphatase Inhibitors, 209th National American Chemical Society Meeting, Annaheim, CA, MEDI 14.

Burke, Jr., T.R., et al. (1995) Conformationally Constrained Phosphotyrosyl Mimetics Designed as Monomeric SH2 Domain Inhibitors, J. Med. Chem. (Exhibit I).

Corey, S.D., et al. (1993) EPSP Synthase Inhibitor Design III. Synthesis & Evaluation of a New 5-Oxamic Acid Analog of ESPS which Incorporates a Malonate Ether as a 3-Phosphate Mimic, Bioorg. Med. Lett. 3:2857–2862.

Domchek, S.M., et al. (1992) Inhibition of SH2 Domain/Phosphoprotein Association by a Nondrolyzable Phosphonopeptide, Biochemistry 31:9865–9870.

Kole, H., et al. (1995?) Protein–Tyrosine Phosphatase Inhibition by a Peptide Containing the Phosphotyrosyl Mimetic, L-O-Malonyltyrosine (L-OMT), Biochem. Biophys. Res. Commun.

Marzabadi, M.R., et al. (1992) Design & Synthesis of a Novel EPSP Synthase Inhibitor Based on its Ternary Complex with Shikimate-3-Phosphate and Glyphosate, Bioorg. Med. Chem. Lett. 2:1435–1440.

Miller, M.J., et al. (1993) EPSP Synthase Inhibitor Design II. The Importance of the 3-Phosphate Group for Ligand Binding at the Shikimate-3-Phosphate Site & the Identification of 3-Malonate Ethers as Novel 3-Phosphate Mimetics, Bioorg. Med. Chem. Lett. 7:1435–1440.

Nomizu, M., et al. (1994) Synthesis of Phosphonomethyl-Phenylalanine and Phosphotyrosine Containing Cyclics Peptides as Inhibitors of Protein Tyrosine Kinase/SH2 Interactions, Tetrahedron 50:2691–2702.

Nomizu, M., et al. (1994) Synthesis and Structure of SH2 Binding Peptides Containing 4-Phosphonomethyl-Phenylalanine and Analogs, Peptide Chemistry: Proceedings of the 31st Japanese Symposium. Kobe: Protein Research Foundation, Osaka, Japan.

Otaka, A., et al. (1993) Synthesis and Structure Activity Studies of SH2 Binding Peptides Containing Hydrolytically Stable Analogs of O-Phosphotyrosine, Peptides: Chemistry and Biology: Proceedings of the Thirteenth American Peptide Symposium. Edmonton, Alberta, Canada: ESCOM Publishers, Leiden, The Netherlands.

(List continued on next page.)

Primary Examiner—Cecilia J. Tsang
Attorney, Agent, or Firm—Morgan & Finnegan, LLP

[57] ABSTRACT

The present invention relates to non-phosphorus containing O-malonyltryrosyl compounds, derivatives thereof, uses of the O-malonyltryrosyl compounds in the synthesis of peptides, and O-malonyltryrosyl compound-containing peptides. The O-malonyltyrosyl malonyltyrosyl compounds and O-malonyltryrosyl compound-containing peptides of the present invention are uniquely stable to phosphotases, capable of crossing cell membranes, suitable for application to peptide synthesis of O-malonyltryrosyl compound-containing peptides, and amenable to prodrag defivatization for delivery into cells. The present invention also provides for O-malonyltryrosyl compound-containing peptides which exhibit inhibitory potency against binding interactions of receptor domains with phosphotyrosyl-containing peptide ligands.

11 Claims, 3 Drawing Sheets

OTHER PUBLICATIONS

Shoelson, S.E., et al. (1991) Solid Phase Synthesis of Nonhydrolyzable Phosphotyrosyl Peptide Analogs with N(alpha)–Fmoc–(O,O–di–tert–butyl)phosphono–para–methylphenylalanine, *Tetrahedron Letters* 32;6061–6064.

Sikorski, J.H., et al. (1993) EPSP Synthase: the Design and Synthesis of Bisubstrate Inhibitors Incorporating Novel 3–Phosphate Mimics, *Phosphorus, Sulfur, and Silicon* 76:115–118.

Sikorski, J.H., et al. (1990) An Enzyme–Targeted Herbicide Design program Based on EPSP Synthase: Chemical Mechanism and Glyphosate Inhibition Studies, *Chem Aspects Enzyme Biotechnol.* [Proc. Tex. A&M Univer., Iuccp Annu. Symp.].

Smyth, M.S., et al. (1992) A general Method for the Preparation of Benzylic Alpha, Alpha–Difluorophosphonic Acids; Non–Hydrolyzable Mimetics of Phosphotyrines, *Tetrahedron Lett.* 33:4137–4140.

Sternbach, David D., Progress Toward Small Molecule Inhibitors of src SH3–SH2 Phosphoprotein Interactions. 209th American Chemical Society Meeting, Anaheim, California, Apr. 2–6, 1995. MEDI 144.

Tan, Y.H., (1993) Yin and Yang of Phosphorylation in Cytokine Signaling, *Science* 262:376–377.

O-MALONYLTRYROSYL COMPOUNDS, O-MALONYLTRYROSYL COMPOUND-CONTAINING PEPTIDES, AND USE THEREOF

FIELD OF THE INVENTION

The invention relates to non-phosphorus containing O-malonyltryrosyl compounds, derivatives thereof, O-malonyltryrosyl compound-containing peptides, pharmaceutical compositions comprising said peptides, and their use as pharmaceutically active agents. The invention also provides for O-malonyltryrosyl compound-containing peptides which exhibit inhibitory potency against binding interactions of receptor domains and against protein-tyrosine phosphatases.

BACKGROUND OF THE INVENTION

Aberrant cellular signal transduction can cause or accentuate a variety of disease processes including immune dysfunction, cancer, and diabetes. For this reason, cell signaling pathways have become targets for the development of new therapeutic agents (Brugge, J.S., Science 260:918–919 (1993); Brunton, V. G. and Workman, P.; Cancer Chemother Pharmacal 32:1–19 (1993)). One of the most intensely studied areas of cellular signal transduction is the area of phosphotyrosyl-dependent pathways. Particularly important in phosphotyrosyl dependent pathways is the strategic role of phosphotyrosyl (pTyr) residues, which appear to serve as molecular switches that can both activate and inactivate downstream signaling processes. (Panayotou, G. and Waterfield, M.D., Bioessays 15:171–177 (1993)). Binding of ligands to the extracellular domain of growth factor receptors, including the insulin receptor, triggers their intercellular protein-tyrosine kinase (PTK) domains resulting in substrate phosphorylation on tyrosine and further signal transduction. (Brunton, V. G. and Workman, P.; Cancer Chemother Pharmacal 32:1–19 (1993)).

Specifically, signal transduction by pTyr-dependent mechanisms relies on a complex triad of interactions. This includes PTKs, which generate pTyr residues, frequently in response to external stimuli, such as binding of growth hormones to cell surface receptors. A second signaling component is assumed by protein-tyrosine phosphatases (PTPs), which remove pTyr phosphates, and may play either positive or negative roles in the overall signal transduction. The third leg of the triad is assumed by Src homology 2 (SH2) domain-mediated binding of secondary signaling proteins to pTyr residues contained within protein structures. The actions of PTKs are counterbalanced by protein-tyrosine phosphatases (PTPs) which hydrolyze pTyr phosphate esters (Walton, K. M.; Dixon, J. E., Ann. Rev. Biochem. 62:101–120 (1993), and which would conceptually be expected to act as inhibitory regulators of PTK-mediated signaling. It has previously been suggested that PTPs may also be positive signal effectors in several systems (Tan, Y. H., Science 262:376–377 (1993)). For example, PTPα, CD45 and p80cdc25 are PTPs which can activate the PTKs, p60$^{src}$ and p56$^{lck}$ and the serine-threonine kinare p34cdc2 (Morla, A. O., et al., Cell 58:193–203 (1989)) respectively, perhaps by dephosphorylating inhibitory pTyr residues. PTPs also appear to be required for the mitogenic effects of some cytokines, such as interleukin-4 (IL-4) (Miresluis, A. R.; Thorpe, R., J Biol Chem 266:18113–18118 (1991)) and for some interferons (Igarashi, K., et al., Mol Cell Biol 13:3984–3989 (1993)). PTPs may also contribute directly to disease processes, as exemplified by the insulin receptor PTK, which is activated by autophosphorylation following binding of insulin to the extracellular ligand-binding domain, and where hydrolysis of these activating pTyr residues by PTPs could potentially exacerbate diabetic conditions (Sale, G. J., Advances in Protein Phosphatases 6:159–186 (1991)).

In spite of the potential value which PTP inhibitors may present for the study of signal transduction pathways and for therapeutic intervention, relatively little has been reported on the development of such agents. Several metal-containing PTP inhibitors are known, including vanadate, oxovanadium complexes (Posner, B. L, et al., J Biol Chem 269:4596–4604 (1994); Watanabe, H., et al., J. Med Chem. 37:876–877 (1994)) and gallium nitrate (Berggren, M. M., et al., Cancer Res 53:1862–1866 (1993)) as well as large, highly charged molecules such as suramin (Ghosh, J.; Miller, R. A., Biochem Bipohys Res Commun, 194:36–44 (1993)) and melittin (Errasfa, M.; Stern, A., Eru J. Pharmacal 247:73–80 (1993)). All of these agents would be expected to act in a fairly nonspecific fashion. The search for small molecule inhibitors has recently yielded the nitrosoamine-containing fermentation product "dephostatin" (Imoto, M., et al., J. Antibiot 46:1342–1346 (1993)) and the irreversible suicide inhibitors, 4-difluoromethyl phenylphosphate (Wange, R. L., et al., J. Biol. Chem., 270:944–948 (1995)), however both of these latter compounds could potentially generate highly toxic metabolites.

Another approach toward the design of PTP inhibitors relies on the replacement of pTyr residues in PTP peptide substrates with non-hydrolyzable phosphate mimetics. Phosphonic acids are isosteric with parent phosphates, yet are chemically and enzymatically resistant to P-C bond cleavage, making them valuable phosphate mimetics in a variety of biologically relevant contexts (Blackburn, G. M., Chem. Ind. (London) 134–138 (1981); Engel, R. Phosphonic acids and phosphonates as antimetabolites, in the role of phosphonates in living systems. R.L. Hilderbrand, Editor. 1983, CRC Press, Inc: Boca Raton, Fla. p. 97–138). Phosphonomethyl phenylalanine (Pmp) is a phosphonate-based surrogate of pTyr in which the phosphate ester oxygen has been replaced by a methylene unit. Pmp-containing peptides have previously been shown to act as competitive PTP inhibitors (Chatterjee, S., et at., Peptides: Chemistry and Biology, J. E. Rivier and J. A. Smith, Editor. 1992, Escom Science Publishers: Leiden, Netherland, p. 553–555; Zhang, Z. Y., et at., Biochemistry 33:2285–2290 (1994)). Pmp-bearing peptides also bind to Src hornology 2 (SH2) domains similar to the native pTyr-containing peptides, yet with reduced affinity (Domchek, S. M., et at., Biochemistry 31:9865–9870 (1992)). A Pmp derivative, phosphonodifluoromethyl phenylalanine (F$_2$Pmp), was previously developed which bears two fluorines substituted at the alpha methylene (Burke, T. R., Jr., et at., J. Org. Chem. 58:1336–1340 (1993); Burke, T. R., Jr., et at., Tetrahedron Lett. 34:4125–4128 (1993); Smyth, M. S., et at., Tetrahedron Lett. 33:4137–4140 (1992)). It has also been shown that the F$_2$Pmp-containing peptides exhibit enhanced inhibitory potency in PTP assays relative to their Pmp counterparts (Burke, T. R., Jr., et at., Biochem. Biophys. Res. Commun. 204:1148–1153 (1994)). However, F$_2$Pmp-containing peptides are inadequate for use in pharmaceutical compounds, for although the F$_2$Pmp moiety is a valuable new motif for the preparation of PTP inhibitors, its di-ionized character at physiological pH makes it resistant to crossing cell membranes. Because of the inability of F$_2$Pmp-containing peptides to cross cell membranes, tedious microinjections (Xiao, S., et al, J Biol Chem 269:21244–21248 (1994)) or cell permeabilizations (Wange, R. L., et al., *J. Biol. Chem.*, 270:944–948 (1995)) techniques are required. Methods have been reported for the bio-reversible protection of phosphates (for example, Srivastva, D. N.; Farquhar, D., *Bioorganic chemistry* 12:118–129 (1984)) and phosphates (for example, Iyer, R. P., et al., *Tetrahedron Letters* 30:7141–7144 (1989); Freeman, S., et al., *J. Chem. Soc. Chem. Commun.* 875–877; (1991); Mitchell, A. G., et al., *J. Chem. Soc. Perkin Trans. I* (1992); Lombaert, S. D., et at., *J. Med. Chem.* 37:498–511 (1994)), such "prodrug" derivatization is frequently difficult to accomplish and not readily suitable for application to peptide synthesis. Thus, the lability to phosphatases, and the low penetration across cell membranes of the phosphate-containing containing pTyr pharmaeophore, provide two significant limitations to the therapeutic or pharmacological utility of pTyr-based agents. There is therefore a great need for pTyr mimetics which can be prepared as prodrugs amenable for solid-phase peptide synthesis, and which maintain PTP inhibitory potency when substituted into appropriate peptides.

The use of a malonate pharmacophore to mimic phosphate functionality has been described in an unrelated enzyme system (See Marzabadi, M. R., et al., *Bioorg. Med. Chem. Lett.* 2:1435–40 (1992); Corey, S. D., et at., *Bioorg. Med. Chem, Lett*, 3:2857–2862 (1993); Miller, M. J., et al., *Bioorg. Med. Chem. Lett.*, 7:1435–1440 (1993); Sikorski, J. A., et al., *Phosphorus, Sulfur Silicon Relat. Elem.* 76:115–118 (1993)). However, these compounds were not directed at pTyr or related signaling.

One means of modulating PTK dependent signaling is by inhibition of Src homology 2 (SH2) domain binding interactions. Small pTyr containing peptides are able to bind to SH2 domains and compete with larger pTyr peptides or native protein pTyr ligands. Such pTyr peptides are limited in their utility as SH2 domain inhibitors in vivo due to their hydrolyric liability to PTPs and poor cellular penetration of the ionized phosphate moiety. The phosphonate-based pTyr mimetics Pmp and F$_2$Pmp, mentioned above, have been successfully employed for the preparation of PTP-resistant SH2 domain inhibitor peptides, however the problem of cellular penetration remains unsolved for these phosphonate-based compounds.

SH2 domains are homologous sequences of approximately 100 amino acids found in a variety of important signal transducing molecules, where they facilitate a key component of PTK mediated cellular signaling by promoting protein-protein associations. (Margolis, B., *Growth Differ* 3:73–80 (1993); Panayotou, G., et al., *Bioessays* 15:171–177 (1993); and Pawson, T., et al., *Curr Biol* 3:434–442 (1993)). The central roles played by PTKs in a large number of mitogenic signaling cascades (Fantl, W. J., et al., *Ann. Rev. Biochem.*, 453–481 (1993); Fry, M. J., et al., *Protein Sci.* 2:1785–1797 (1993)), and the involvement of aberrant or over-expression of PTKs with several cancers and proliferative diseases (Cantley, L. C., *Cell* 64:281–302 (1991)), has made the development of inhibitors which specifically block the binding of SH2 domains desirable both as biological tools and as potential therapeutic agents. (Burke, T. R., et at., *Drugs of the Future* 17:119–131 (1992); Brugge, J. S., *Science* 260:918–919 (1993)). For SH2 binding domains, interactions are frequently dependent on the presence of a pTyr residue in the bound protein. Among different classes of SH2 domains, a secondary ligand specificity resides within the amino acid sequence neighboring the pTyr residue, particularly in residues toward the C-terminal side, thereby allowing families of SH2 domains to "recognize" specific binding sites on target proteins.

Small pTyr-bearing peptides modeled after these target sequences also bind with high affinity and moderate selectivity to the appropriate SH2 domains, thereby providing a potential means of competitively inhibiting specific SH2 signaling pathways. (Fantl, W.J., et at., *Cell* 69:413–423 (1992); Songyang, Z., et al., *Cell* 72:767–778 (1993).

Accordingly, the present invention overcomes the obstacles of the prior art by providing for the preparation and use of new O-malonyltryrosyl compounds and O-malonyltryrosyl compound-containing peptides which are stable to phosphatases, capable of crossing cell membranes, suitable for application in peptide synthesis, and amenable to prodrug derivatization for delivery into cells. The present invention also provides for O-malonyltryrosyl compounds and derivatives thereof which can be protected in the neutral diester form for enhanced delivery across cell membranes and subsequent esterase-mediated liberation of the active dicarboxylic acid once inside the cell.

The present invention further provides for use of the O-malonyltryrosyl compound-containing compounds in the synthesis of peptides, and for O- malonyltryrosyl compound-containing peptides which exhibit inhibitory potency against binding interactions of receptor domains with pTyr-containing peptide ligands, whose advantages and uses will become apparent from the following objectives of the invention and disclosure.

SUMMARY OF THE INVENTION

The present invention relates to O-malonyltryrosyl compounds and derivatives thereof, the application of O-malonyltryrosyl compounds in pepfide synthesis, and O-malonyltryrosyl compound-containing peptides and uses thereof. The O-malonyltryrosyl compounds, derivatives thereof, and O-malonyltryrosyl compound-containing peptides of the present invention are stable to phosphatases, suitable for application to peptide synthesis of O-malonyltryrosyl compound-containing peptides, and amenable to prodrug derivafization for delivery into cells.

Specifically, the present invention provides for the preparation and use of O-malonyltryrosyl compounds herein designated "OMT". The present invention further provides for the design and preparation of OMT compounds protected in the carboxylie acid diester form, suitable for incorporation into peptides.

The present invention further provides for the design and synthesis of derivatives of OMT, such as, for example, O,O-bis(tert-butyl)-N-Fmoc OMT and monofluoro-OMT.

The present invention also provides for OMT compounds which exhibit inhibitory activity against protein-tyrosine phosphatases (PTPs).

The present invention additionally provides for OMT-containing peptides which exhibit inhibitory potency against protein-tyrosine phosphatase (PTP), or Src homology 2 (SH2) domain binding interactions with phosphotyrosyl-containing ligands.

Specifically, the present invention provides for the preparation and use of OMT-containing peptides which exhibit inhibitory potency against P1-3 kinare C-terminal p85 SH2 domain binding interactions with phosphotyrosyl-containing peptide ligands.

Further, the present invention provides for methods of preparation and use of OMT-containing peptides directed against Src domain binding interactions with phosphotyrosyl-containing ligands.

The present invention further provides the preparation and use of OMT-containing containing peptides directed against Grb SH2 domain binding interactions with phosphotyrosyl-containing ligands.

The present invention further provides for methods of preparation and use of OMT-containing peptides directed against N-terminal SH-PTP 2 SH2 domain binding interactions with phosphotyrosyl-containing ligands.

Further, the present invention provides methods and compositions for treating or preventing disease processes, such as those associated with immune dysfunction, cancer, and diabetes.

The present invention also provides methods of preventing or treating a disease, such as immune dysfunction, cancer, and diabetes, by the administration of a therapeutically effective amount of an OMT-containing peptide.

The present invention also provides methods of preventing or treating cancers by the administration of a therapeutically effective amount of an OMT-containing peptide in combination with toxins, cytotoxic drugs, or irradiation.

The present invention also provides for pharmaceutical compositions for use in the methods described herein.

BRIEF DESCRIPTION OF THE FIGURES

FIGS. 1A and 1B set forth the structures and relative binding sites of (A) arylphosphate and (B) arylmalonate pharmacophores to the p56$^{lck}$ SH2 domain.

FIGS. 2A and 2B set forth the energy minimized structures of $HCF_2PO(O—)_2$ (FIG. 2A) and $CH_2(CO_2—)_2$ (FIG. 2B) bound within the protein tyrosine phosphatase 1B (PTP-1B) catalytic site.

FIG. 3 sets forth the effect of the OMT-peptide Ac-Asp-Ala-Asp-Glu-[L-OMT]-Leu-amide on PTP 1B catalyzed insulin receptor dephosphorylation using $^{32}$P-labeled intact insulin receptor as substrate.

FIG. 4 sets forth the effect of the FOMT-peptide Ac-Asp-Ala-Asp-Glu-[L-FOMT]-Leu-amide on PTP 1B catalyzed insulin receptor dephosphorylation using $^{32}$P labeled intact insulin receptor as substrate.

DETAILED DESCRIPTION OF THE INVENTION

Figure 1B:
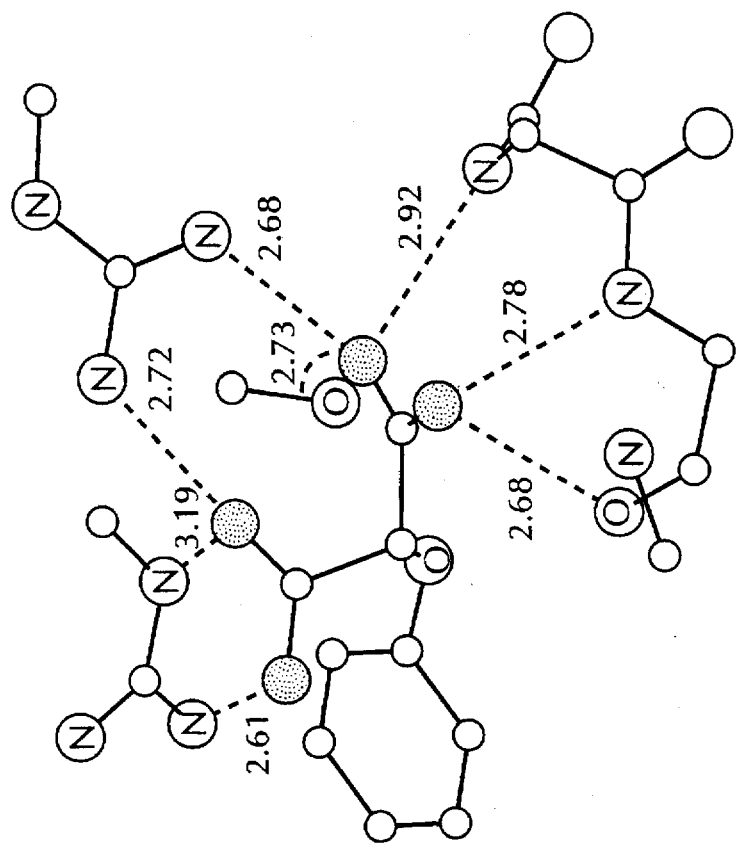
FIGS. 1A and 1B.

The present invention generally provides novel O-malonyltryrosyl compounds, novel O-malonyltyrosyl compound-containing peptides, pharmaceutical compositions comprising said peptides, and their use as pharmaceutically active agents.

More particularly, the present invention provides for the preparation and use of novel O-malonyltyrosyl compounds and derivatives thereof which are stable to phosphatases and capable of crossing cell membranes. The present invention also provides that the new O-malonyltryrosyl compounds and derivatives thereof are amenable to prodrug derivatization for delivery into cells. Derivatization herein refers to derivatization of the O-malonyltryrosyl compound to a diester, thus converting the compound to a cell permeable form.

The present invention relates to O-malonyltryrosyl compounds of the Formula (I):

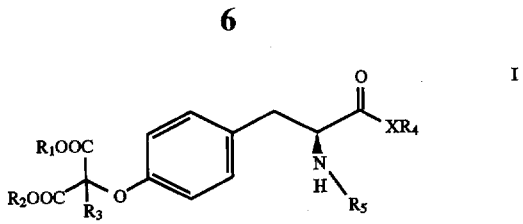

wherein $R_1$, and $R_2$, are independently hydrogen, alkyl, aralkyl, alkaryl, aryl, and heteroaryl;

wherein $R_3$ is hydrogen, halogen, amino, hydroxy, and alkoxy;

wherein X is nitrogen or oxygen;

wherein $R_4$ is hydrogen, alkyl, aralkyl, alkaryl, optionally substituted aryl, and heteroaryl;

wherein $R_5$ is hydrogen, fluorenyl methoxy carbonyl (FMOC), tert-butoxy carbonyl (BOC), and carbobenzoxy (CBZ), carbamoyl, alkyl, amido, aryl, and heteroaryl; with the proviso that substituents of Formula (I) which can be substituted are optionally substituted.

Preferred $R_1$ and $R_2$ substituents of Formula I, can be, for example, tert-butyl, phenyl, and benzyl.

Preferred $R_4$ substituents of Formula I, can be, for example, tert-butyl, benzyl, and pentafluorophenyl.

Alkyls occurring in Formula I can be alkyls which are $C_{1-20}$ alkyls.

When halogens occur in Formula I, the halogens can be chlorine, bromine, or fluorine, and the preferred halogen is fluorine.

When substituted alkyls occur in Formula I, examples of suitable substituents are hydroxy, halogen, alkoxy, haloalkoxy, and alkoxyalkyl; and wherein the alkyl groups and the alkyl groups of the alkaryl and aralkyl groups herein are linear or branched chain, or cyclic having up to 10 carbon atoms.

When substituted heteroaryl groups occur in Formula I, examples of suitable substituents are halogen, nitro, cyano, or haloalkyl groups; and wherein the alkyl, haloalkyl, alkenyl, haloalkenyl, alkoxy, and haloalkoxy groups herein are linear or branched chains, having less than 10 carbon atoms, preferably less than 5 carbon atoms, and the halo substitution in all these groups consists of one or more halogen atoms, which are the same or different, from mono substitution up to complete poly substitution.

The present invention further relates to the application of the compounds of Formula (II) for use in the synthesis of peptides:

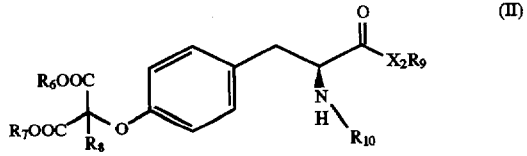

wherein $R_6$ and $R_7$ are independently hydrogen, alkyl, aryl, alkaryl, and ethylenethioalkyl;

wherein $R_8$ is hydrogen, halogen, alkoxy, haloalkoxy, nitro, amido, and substituted amino groups;

wherein $X_2$ is nitrogen or oxygen;

wherein $R_9$ is hydrogen, alkyl, aralkyl, alkaryl, optionally substituted aryl, and heteroaryl;

wherein $R_{10}$ is hydrogen, fluorenyl methoxy carbonyl (FMOC), tert-butoxy carbonyl (BOC), and carbobenzoxy (CBZ), carbamoyl, alkyl, amido, aryl, and heteroaryl; with the proviso that substituents of Formula (II) which can be substituted are optionally substituted.

Preferred $R_9$ substituents of Formula II can be, for example, tert-butyl, benzyl, and pentafluorophenyl.

Alkyls occurring in Formula II can be alkyls which are $C_{1-20}$ alkyl and $C_{1-6}$ alkyl. Aryls occurring in Formula II can be aryls which are $C_{6-10}$ aryl.

When substituted alkyls occur in Formula II, examples of suitable substituents are hydroxy, halogen, alkoxy, haloalkoxy, and alkoxyalkyl; and wherein the alkyl groups and the alkyl groups of the alkaryl and aralkyl groups herein are linear or branched chain, or cyclic having up to 10 carbon atoms.

When substituted heteroaryl groups occur in Formula II, examples of suitable substituents are halogen, nitro, cyano, or haloalkyl groups; and wherein the alkyl, haloalkyl, alkenyl, haloalkenyl, alkoxy, and haloalkoxy groups herein are linear or branched chains, having less than 10 carbon atoms, preferably less than 5 carbon atoms, and the halo substitution in all these groups consists of one or more halogen atoms, which are the same or different, from mono substitution up to complete poly substitution.

The present invention further relates to peptides of the Formula (III):

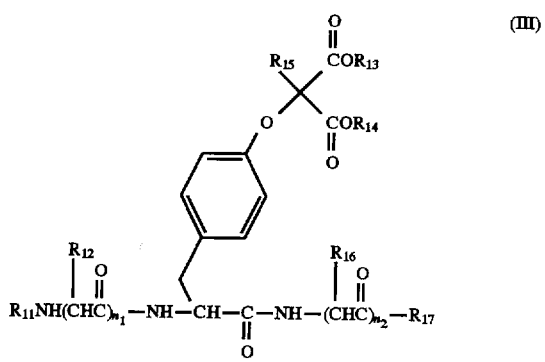

wherein $R_{11}$ is hydrogen, acetyl, alkanoyl, alkyl, aryl, aralkyl, alkaryl, or polyethyleneoxy;

wherein $R_{12}$ and $R_{16}$ are residues of amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, or derivatives thereof, and also a residue of a unit derived from the O-malonyltryrosyl compounds of Formula II;

wherein $R_{13}$ and $R_{14}$ are independently hydrogen, alkyl, and ethylenethioalkyl;

wherein $R_{15}$ is hydrogen, halogen, alkoxy, haloalkoxy, nitro, amido, and substituted amino groups;

wherein $R_{17}$ is hydroxy, $NH_2$, O-alkyl, O-aryl, O-aralkyl, O-alkaryl, N-polyethyleneoxy; and wherein $n_1$ and $n_2$ may be the same or different, are zero, or 1–10, but wherein $n_1$ and $n_2$ are not zero at the same time;

with the proviso that substituents of Formula (III) which can be substituted aare optionally substituted.

Alkyls occurring in Formula III can be alkyls which are $C_{1-20}$ alkyl.

Aryls occurring in Formula III can be aryls which are $C_{6-10}$ aryl.

When substituted alkyls occur in Formula III, examples of suitable substituents are hydroxy, halogen, alkoxy, haloalkoxy, and alkoxyalkyl; and wherein the alkyl groups and the alkyl groups of the alkaryl and aralkyl groups herein are linear or branched chain, or cyclic having up to 10 carbon atoms.

When substituted heteroaryl groups occur in Formula III, examples of suitable substituents are halogen, nitro, cyano, or haloalkyl groups; and wherein the alkyl, haloalkyl, alkenyl, haloalkenyl, alkoxy, and haloalkoxy groups herein are linear or branched chains, having less than 10 carbon atoms, preferably less than 5 carbon atoms, and the halo substitution in all these groups consists of one or more halogen atoms, which are the same or different, from mono substitution up to complete poly substitution.

When $R_{12}$ and $R_{16}$ of Formula III are independently amino acids or derivatives thereof, and one or more of the amino acids is aspartic acid and/or glutamic acid, the preferred sidechains of the aspartic acid and/or glutamic acid moieties are independently n-butyl ester, n-alkyl, or aryl.

When $R_{12}$ and $R_{16}$ of Formula III are independently peptides, the amino acid sequence may be a linear or branched chain, and may consist of any number of amino acids, usually from about three to thirty amino acids, the preferred length being 5–10 amino acids. The amino acid sequence of the peptide depends upon the particular use of the peptide. For example, the design of a peptide for use as an inhibitor of receptor binding will be directed toward the amino acid sequence of the particular receptor domain, and may vary greatly between reeeptors.

Specific but not limiting examples of peptides of Formula III useful in the present invention include the following:

(1) peptide D-X-V-P-M-L (SEQ ID NO. 1), directed towards inhibition of the binding of the PI-3 kinase C-terminai p85 SH2 domain with phosphotyrosyl-containing peptide ligands, wherein X is the residue of a compound of Formula II;

(2) peptide Q-X-E-E-I-P (SEQ ID NO. 2), directed towards inhibition of the binding of the Src SH2 domain with phosphotyrosyl-containing peptide ligands, wherein X is the residue of a compound of Formula II;

(3) peptide N-X-V-N-I-E (SEQ ID NO. 3), directed towards inhibition of the binding of the Grb2 SH2 domain with phosphotyrosyl-containing peptide ligands, wherein X is the residue of a compound of Formula II; and (4) peptide L-N-X-I-D-L-D-L-V (SEQ ID NO. 4), directed towards inhibition of the binding of the N-terminal SH-PTP2 SH2 domain with phosphotyrosyl-containing peptide ligands, wherein X is the residue of a compound of Formula II.

The O-malonyltryrosyl compounds and O-malonyltryrosyl compound-containing peptides of the present invention may exist in a free, i.e. unprotected, or a protected form. The protected form herein refers to compounds wherein one or more reactive groups, e.g. N-terminal amino groups or —OH groups, are covered by a protecting group. Suitable protecting groups are any of those known in the art of peptide chemistry, such as N—, carboxy-, and O— protecting groups. The preferred form of the O-malonyltryrosyl compound-containing peptides of the present invention is the diester form, wherein the carboxyl groups are in a neutral state, allowing for passage through cell membranes. The carboxylic acid diester form, alkyl or other suitable prodrug esters, may be considered "prodrug", i.e. protected forms of the compound which are useful as pharmaceuticals.

The peptides of the present invention, whether they are in free or protected form, may exist as salts or as complexes. Acid addition salts may be formed with organic acids, polymeric acids, and inorganic acids, for example. Such acid addition salt forms include inter alia the hydrochlorides and acetates. Complexes are herein defined as compounds of known type, formed on addition of inorganic substances, such as inorganic salts or hydroxides such as Ca— and Zn— salts, and/or on addition of polymeric organic substances.

The present invention further provides methods and compositions for preventing or treating diseases. Particular non-limiting examples of diseases include immune dysfunction, cancer, and diabetes. Specifically, this invention provides for the use of the compounds and compositions of the present invention to inhibit binding interactions of receptor domains with phosphotyrosyl-containing ligands for treating or preventing the disease processes associated with immune dysfunction, cancer, or diabetes. This invention also provides pharmaceutical compositions comprising the same.

More particularly, the present invention provides methods of treating diabetes by administration of a therapeutically effective amount of an O-malonyltyrosyl compound-containing peptide which, for example, exhibits inhibitory potency against the binding interactions of the SH2 domain with phosphotyrosyl-containing ligands.

The present invention further provides methods of preventing or treating a disease by the administration of a therapeutically effective amount of an O-malonyltyrosyl compound-containing peptide.

The present invention also provides methods of preventing or treating diseases by the administration of a therapeutically effective amount of an O-malonyltyrosyl compound-containing peptide in combination with chemotherapeutic agents, toxins, or irradiation. Examples of chemotherapeutic agents are known to those skilled in the art and include, but are not limited to, bleomycin, mitomycin, cyclophosphomide, doxorubicin, paclitaxel, and cisplatin.

In one embodiment of the invention, the O-malonyltryrosyl compound-containing peptides are administered in a pharmaceutically acceptable carrier. A pharmaceutically acceptable carrier encompasses any of the standard pharmaceutical carriers such as sterile solution, tablets, coated tablets and capsules. Such carriers may typically contain excipients such as starch, milk, sugar, certain types of clay, gelatin, stensic acid, talc, vegetable fats or olis, gums, glycols, or other known excipients. Such carriers may also include flavor and color additives and other ingredients.

The administration of the compound may be effected by any of the well known methods, including but not limited to, oral, intravenous, intramuscular, and subcutaneous administration. The preferred method of administration is intravenous.

In the practice of the methods of this invention, the amount of the O-malonyltyrolsyl compound-containing peptide incorporated in the composition may vary widely. Methods for determining the precise amount depend upon the subject being treated, the specific pharmaceutical carrier, the route of administration being employed, the frequency with which the compound is to be administered, and whether the composition is administered in conjunction with a chemotherapeutic agent and/or irradiation treatment.

The present invention provides novel O-malonyltryrosyl compounds and O-malonyltyrosyl compound-containing peptides which do not exhibit the problems which presently exist in compounds which have similar applications.

The phosphate-containing pTyr pharmacophore demonstrates lability to phosphatases and low penetration across cell membranes, which are two significant limitations to the therapeutic and pharmacological utility of pTyr-based agents which the practice of the present invention has overcome.

Previously, PTP inhibitors were designed for replacement of the pTyr residue in PTP-substrate peptides. This was accomplished by modifying peptide substrates so as to render them incapable of undergoing chemical transformation by PTP. Replacement of the pTyr residue in PTP-substrate peptides, with the non-hydrolyzable pTyr mimetic, Pmp 2 (Burke, T. R., Jr. et al., *Synthesis* 11:1019–1020 (1991)), resulted in peptides which are competitive PTP inhibitors (Chatterjee, S., et al., Peptides: Chemistry and Biology, J. E. Rivier and J. A. Smith, Editor, 1992, Escom Science Publishers: Leiden, Netherlands. p. 553–555; Zhang, Z. Y., et al., *Biochemistry* 33:2285–2290 (1994)). Pmp differs from pTyr in having a methylene substituted for the tyrosyl 4'-ester oxygen. It was previously shown that substitution of the Pmp residue in one such hexameric inhibitor peptide with $F_2$Pmp 3 (Burke, T. R., Jr., et al., *J. Org. Chem.* 58:1336–1340 (1993); Burke, T. R., Jr., *Tetrahedron Lett.* 34:4125–4128 (1993); Smyth, M. S. and Burke, T. R., Jr., *Tetrahedron Lett.* 35:551–554 (1994)) resulted in a 1000-fold increase in inhibitory potency ($IC_{50}$=100 nM against PTP 1B) (Burke, T. R., et al., *Biochem. Biophys. Res. Commun.* 204:129–134(1994)). Because the difluorophosphonate moiety is di-ionized at physiological pH (Smyth, M. S., et al., *Tetrahedron Lett.* 33:4137–4140 (1992)), transport across cell membranes was compromised and cellular studies of $F_2$Pmp-containing peptides resorted to membrane permeabilization (Wange, R. L., et al., *J. Biol. Chem.* 270:944–948 (1995)) or microinjection (Xiao, S., et al., *J.Biol. Chem.* 269:21244–21248 (1994)) techniques. While prodrug protecting groups have been developed for phosphates (Srivastva, D. N. and Farquhar, D., *Bioorganic Chemistry* 12:118–129 (1984); McGuigan, C., et al., *Bioorg. Med. Chem. Lett.* 2:701–704 (1992); Perigaud, C., et al., *Bioorg. Med. Chem. Lett* 3:2521–2526 (1993); Farquhar, D., et al., *J. Med. Chem.* 38:488–495 (1995)) and phosphonates (Freeman, S., et al., *J. Chem. Soc. Chem. Commun.* 875–877 (1991); Lombaert, S. D., et al., *J. Med. Chem.* 37:498–511 (1994)), these protecting groups have not yet been extended to $F_2$Pmp-containing peptides, where synthetic challenges exist.

The present invention overcomes the deficiencies of the fluorine-containing peptides of the prior art by providing for the design and synthesis of nonhydrolyzable non-phosphorus-based O-malonyltryrosyl compounds. For example, Pmp 2 and its monofluoro (FPmp 3) and difluoro ($F_2$Pmp 4) analogues have been shown to retain SH2 domain binding potency when substituted into appropriate peptides, yet are not hydrolyzed by phosphatases. (See Domchek, S. M., et al., *Biochemstry* 31:9865–9870 (1992); Burke, T. R., Jr., et al., *Biochemistry* 33:6490–6494 (1994)). Since the phosphonate group is ionized at physiological pH, (Smyth, M. S.,et al., *Tetrahedron Lett.* 33:4137–4140 (1992)) these peptides show limited penetration of cell membranes. $F_2$Pmp-containing peptides have been successfully used in cell-based systems, however only when cells which were made permeable (Wange, R. L., et al., *J. Biol. Chem.* 270:944–948 (1995)) or microinjection techniques (Xiao, S., et al., *J. Biol. Chem.* 269:21244–21248 (1994)) were employed for these studies. Accordingly, there is a need for synthetic peptides which are both nonhydrolyzable and able to penetrate cell membranes.

The literature contains several examples of bio-reversible protection of phosphate (Srivastva, D. N. and Farquhar, D., *Bioorganic Chemistry* 12:118–129 (1984)) and phosphonates, (Iyer, R.P., et al., *Tetrahedron Letters* 30:7141–7144 (1989); Freeman, S., et al., *J. Chem. Soc. Chem. Commun.* 875–877 (1991); Mitchell, A. G., et al., *J. Chem. Soc. Perkin Trans. I* (1992); Lombaert, S. D., et al., *J. Med. Chem.* 37:498–511 (1994)) however such "prodrug" derivatization is frequently difficult to accomplish, not readily applicable to peptide synthesis and has not yet been extended to F2Pmp species. Based on prior findings of Sikorski, et al. that the malonate moiety can mimic a phosphate structure in EPSP (5-enolpyruvoyl-shikimate-3-phosphate) synthase inhibitors, (See Miller, M. J., et al., *Bioorg. Med. Chem. Lett.* 4:2605–2608 (1994)), the compound L-O-malonyltyrosine (L-OMT) was designed and synthesized by the methods of the present invention. L-OMT improves upon the prior compounds used to replace pTyr in that L-OMT is amenable to prodrug derivatization. L-OMT was designed by replacing the phosphate group of the pTyr residue with a malonate dicarboxylic acid structure. As stated previously, the advantage of L-OMT over former phosphonate-based analogues such as F$_2$Pmp is that preparation of OMT as its carboxylic acid diester affords one potential means of prodrug protection. The malonyl structure of OMT contains two carboxylic acids instead of the phosphate group and, as such, it can be readily protected as the di-ester for delivery across cell membranes. One inside the cell, esterase-mediated cleavage of the esters liberate the active di-acid form.

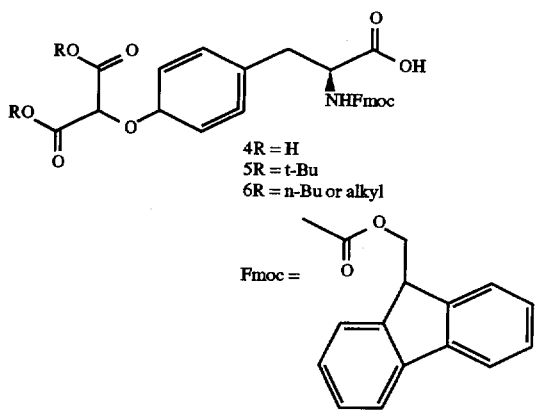

4 R = H
5 R = t-Bu
6 R = n-Bu or alkyl

Fmoc =

The present invention further provides for analogues of OMT having the formulas 5 and 6, shown above, suitably protected for incorporation into peptides by solid-phase synthesis. The present invention demonstrates that poptide synthesis using O,O-bis(tert-butyl)-N-Fmoc OMT formula 5, as described in Example 6, resulted in simultaneous removal of tert-butyl groups during acid-catalyzed cleavage from the resin, and provides OMT-peptides in which the malonate carboxyls are in the free, biologically active acid form. Alternatively, solid-phase peptide synthesis using n-butyl or alkyl esters in place of tert-butyl esters (compounds of formula 6) resulted in final peptides which retain the malonate diester protection. This diester form may be considered a "prodrug" of OMT in that the carboxyl groups are in a neutral form, allowing passage through cell membranes. Liberation of the biologically active, free acid form can then occur by esterase-mediated hydrolysis of the ester functionalities inside the cell.

The present invention also provides for an analogue of OMT, herein designated monofluoro-OMT (FOMT), the synthesis of which is described in Example 7. The present invention further describes a novel use for L-OMT in the synthesis of SH2 domain inhibitory peprides. The process of designing and synthesizing OMT containing, SH2 domain inhibitory peptides of the present invention initially involved the examination of phosphatase resistant amino acid analogues which could serve as a mimetic of pTyr in SH2 binding interactions. The initial examination was based on the knowledge of the hydrolyric lability of tyrosine phosphate to cellular PTPs (See Walton, K. M., et al., *Ann. Rev. Biochem.* 62:101–120 (1993)). Pmp is a phosphonate homologue of pTyr wherein the phosphate ester oxygen has been replaced by a methylene. A protected form of Pmp suitable for incorporation into peptides by solid phase synthesis was developed (See Burke, T. R., et al., *Synthesis* 11:1019–1020 (1991); Shoelson, S. E., et al., *Tetrahedron Lett.* 32:6061–6064 (1991)). The SH2 inhibitory potency of a Pmp-containing peptide corresponding to the sequence surrounding Tyr-315 of the mouse polyoma mT antigen prepared with this reagent was then examined. A two-fold loss of potency was observed for the protected form of Pmp (ID$_{50}$=7.2 μM) as compared with the corresponding pTyr-containing pepride (ID$_{50}$=3.6 μM) (See Domehek, S. M., et al., *Biochemistry* 31:9865–9870 (1992)). Based on this determination, new analogues of Pmp were designed which bore either one fluorine (FPmp)or two fluorines (F$_2$Pmp) on the methylene bridge. (See Burke, T. R., et al., *J. Org. Chem.* 58:1336–1340 (1993); Burke, T. R., et al., *Tetrahedron Lett* 34:4125–4128 (1993); Otaka, A., et al., *Tetrahedron Lett* 34:7039–7042 (1993); and Smyth, M. S., et al., *Tetrahedron Lett.* 35:551–554 (1994)). The inhibitory potencies of the fluorinated Pmp-s were enhanced relative to the parent Pmp. (See Burke, T. R., et al., *Biochemistry* 33:6490–6494 (1994)). The F$_2$Pmp-containing peptides were studied in intact cells. (See Xiao, S., et al., *J. Biol. Chem.* 269:21244–21248 (1994); Wange, R. L., et al., *J. Biol. Chem.* 270:944–948 (1995)). Because the fluorinated Pmp-containing peptides do not have the ability to cross cell membranes, artificial means were required to introduce them into the cell. This lack of cell permeability again emphasizes the significant limitation of phosphonate-based SH2 domain inhibitors as pharmacological tools and as therapeutics. The practice of the present invention improves upon the fluorinated Pmps by providing for a non-phosphorus-based mimetic of pTyr, herein designated O-malonyltyrosyl (OMT), which uses a malonate group in place of the phosphonate or phosphate portion.

The present invention further provides for the preparation and use of OMT-containing peptides which exhibit PTP or SH2 inhibitory potency against binding interactions of receptor domains with phosphotyrosyl-containing ligands. Specific examples of peptides exhibiting PTP or SH2 domain inhibitory potency include, but are not limited to, OMT-containing peptides exhibiting inhibitory potency against the PI-3 kinase C-terminal p85 SH2 domain, the Src SH2 domain, the Grb SH2 domain, and the N-terminal SH-PTP2 SH2 domain.

Generally, the SH2 inhibiting peptides of the present invention were prepared by incorporating OMT into each of four SH2 domain inhibitory peptides using solid-phase peptide techniques and the protected analogue (L)-N$^{60}$-fmoc-O'-[(O",O"-(tertbutyl)malonyl] tyrosine (See Ye, B. and Burke, T. R., Jr., Tetrahedron Lett. (in review)). OMT-residues can potentially be protected in the neutral diester form for delivery across cell membranes and subsequent esterase-mediated liberation of the active dicarboxylic acid once inside the cell. Example 8 describes the preparation and synthesis of four OMT-containing peptides against the following SH2 domains; The PI-3 kinase C-terminal p85 SH2 domain (Ac-D-[L-OMT]-V-P-M-L-amide; IC$_{50}$=14.2 μM (SEQ. ID. NO. 1)); the Src SH2 domain (AC-Q-[L-OMT]-X-E-E-I-P-amide; IC$_{50}$>200 μM (SEQ. ID. NO. 2)); the Grb2 SH2 domain (Ac-N-[L-OMT]-V-N-I-E-amide; IC$_{50}$>600 μM (SEQ. ID. NO. 3)) and the N-terminal SH-PTP2 SH2 domain (Ac-L-N-[L-OMT]-I-D-L-D-L-V-amide; IC$_{50}$=22.0 μM (SEQ. ID. NO. 4)). SH2 domain binding assays were conducted for each of the four peptides, generating the IC$_{50}$ values set forth above. The IC$_{50}$ values indicate a significant degree of selectivity between SH2 domains, with the OMT-containing peptides having reasonable affinity for the p85 and SH-PTP2 SH2 domains but not for the Src and Grb SH2 domains. The $IC_{50}$ value for the SH-PTP2 SH2 domain is equivalent to the previously observed for the corresponding $F_2Pmp$-containing peptide.

Table 1 sets forth the inhibition constants of peptides identical to the four OMT-containing peptides referred to above, except either pTyr or L-$F^2Pmp$ was substituted in place of the OMT moiety. The values demonstrate that OMT-peptide Nos. 7 and 8 are essentially inactive in Src or Grb2 binding assays, respectively. Alternatively, moderate affinity for 6 is indicated against the p85 SH2 domain ($IC_{50}=14.2$ µM), although potency is significantly reduced relative to the corresponding pTyr-peptide ($IC_{50}=0.15$ µM) or L-$F_2Pmp$-peptide ($IC_{50}=0.17$ µM). (See Burke, T. R., Jr., et al., *Biochemistry* 33:6490–6494 (1994)).

Table 1 also indicates the potency of OMT-peptide no. 9 against the SH-PTP2 SH2 domain. While the absolute magnitude of inhibition ($IC_{50}=22$ µM) is of the same order as that seen with the p85 directed L-OMT peptide no. 6, in this latter example the L-OMT peptide suffered a 200 fold loss of potency relative to either the pTyr or $F_2Pmp$ peptides. On the other hand SH-PTP2:peptide no. 9 shows no loss of potency relative to the corresponding L-$F_2Pmp$ peptide ($IC_{50}=23$ µM). (See Xiao, S., et al., *J Biol Chem* 269:21244–21248 (1994)). This is significant as the ability of the L-$F_2Pmp$ peptide to block SH-PTP2 mediated mitogenic signaling in rat 1 fibroblasts was previously demonstrated (See Xiao, S., et al., *J Biol Chem* 269:21244–21248 (1994) suggesting that the L-OMT peptide no. 9 may also possess sufficient potency to elicit a measurable effect in cellular assays.

The interaction of the SH2 domain of the OMT residue of the present invention was compared with that of a native pTyr pharmacophore using molecular modeling studies. (See Example 2 and FIGS. 1A and 1B). Although the phosphate and malonate structures are chemically quite different, and the malonate group occupies approximately 18% more volume than the phosphate (See FIGS. 1A and 1B), their interactions with the SH2 domain are remarkably similar, and both structures can be accommodated while maintaining nearly identical SI-I2 domain geometries, demonstrating that OMT is able to bind to SH2 domains in a manner similar to pTyr residues.

The disparity observed in binding potencies of OMT peptides directed against the different SH2 domains may indicate that the OMT residue is bound differently in the pTyr pockets of the respective SH2 domains. Potency differences may also reflect larger discrepancies in the overall mode of binding of peptide ligands. For example, binding of pTyr peptides to SH2 domains of the Src family have been shown to employ pronounced "two pronged" interactions between the SH2 domain and pTyr and a second hydrophobic pocket located 3 residues C-terminal to the pTyr residue. It could be anticipated that the high contribution of the pTyr binding to the overall peptide-SH2 domain interaction would amplify any loss of potency brought about by a pTyr mimetic. Alternatively, SH2 domains such as SH-PTP2 appear to exhibit peptide-SH2 domain binding interactions distributed over a more extended region. Since the contribution of the pTyr binding to the total binding of the peptide ligand may be less important, loss of affinity at the pTyr binding site may be better tolerated, and a higher retention of potency may be observed for peptides employing pTyr mimetics.

Specificity is a desirable attribute in the development of SH2 domain inhibitors. It has been previously reported that depending on the SH2 domain, peptides bearing the pTyr mimetic F2Pmp 3 can exhibit either enhanced or reduced potency relative to parent pTyr-bearing peptides. (See Burke, T. R., Jr., et al., *Biochemistry* 33:6490–6494 (1994)). This potentially indicated that a measure of selectivity may be achieved by differences in binding at the pTyr site.

A second desired feature of SH2 domain inhibitors is bioavailability. Prodrug delivery of the diester-protected O-malonyltryrosyl compound-containing peptides of the present invention through cell membranes will contribute significantly to the development of cell-permeable inhibitors.

EXAMPLES

The Examples herein are meant to exemplify the various aspects of carrying out the invention and are not intended to limit the scope of the invention in any way.

Example 1

Peptide Synthesis

The tyrosine phosphate mimicking amino acid X=L-OMT was incorporated into the EGFRS88-993 segment, D-A-D-E-X-L, using solid-phase synthesis with Fmoc chemistry. The amino acid Fmoc-L-OMT(tert-butyl)$_2$-OH was synthesized according to a published method (Ye, B. and Burke, T. R., Jr., *Tetrahedron Lett.* (in review)). The peptide was prepared using PAL resin (Albericio, F., et al., *J. Org. Chem.* 55:3730–3743 (1990)), DIPCDI/HOBT coupling reagents, and 20% piperidine/DMF for Fmoc deprotection. The resin-bound protected peptides were acetylated with 10% 1-acetylimidazole/DMF. The peptide Ac-D-A-D-E-[L-OMT]-L-amide was obtained in one step by simultaneous cleavage from the resin and deprotection with TFA containing 5% each (v/v) of ethanedithiol, m-cresol, thioanisole and water. The peptides were purified by reverse phase HPLC under the following conditions: Vydac $C_{18}$ column (10×250 mm); solvent gradient: A:0.0555 TFA in H2O, B: 0.5% TFA in 90% acetonitrile in $H_2O$, gradient (B%): 10–55% over 30 minutes; flow rate: 2.5 mL/minute; UV detector: 220 nm; retention time: 14.5 minutes. FABMS (M+H)+868.3 (calcd. 868.3). Amino acid analysis: Asp (1.98), Glu (1.00), Ala (1.01), Leu (1.02); OMT could not be determined by this analysis.

Example 2

Molecular Modelling

Figure 2B:
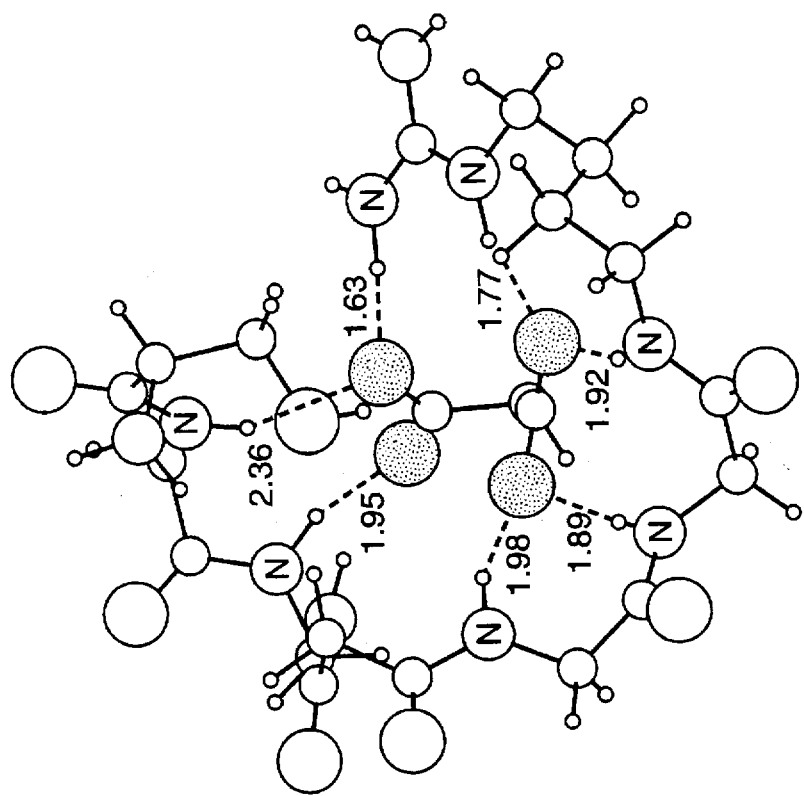
FIGS. 2A and 2B.
Figure 2A:
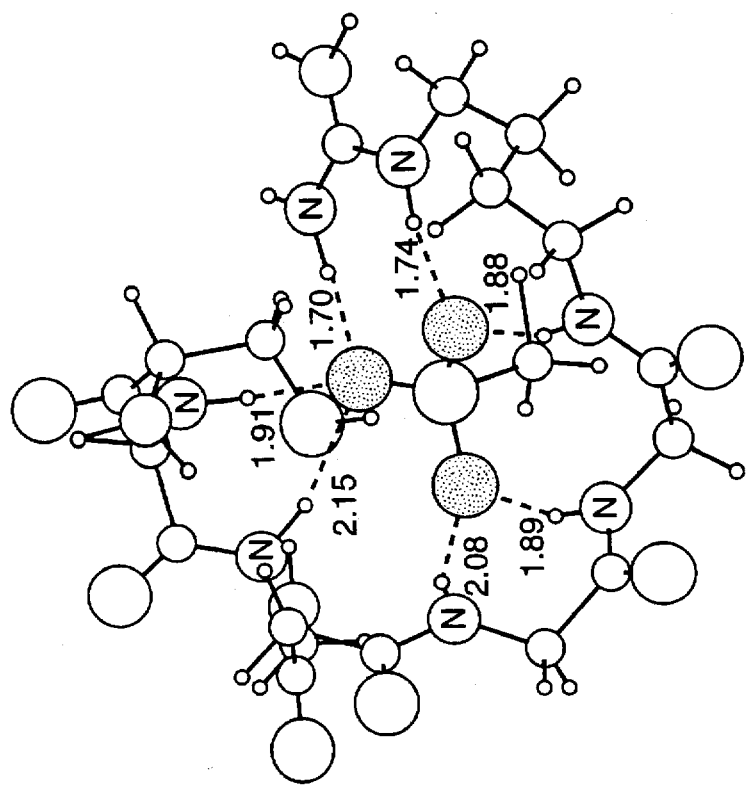

Structures of a difluoromethylphosphonate group [$HCF_2PO(O-)_2$] and a malonate group [$CH_2(CO_2-)_2$], complexed within the catalytic site of the PTP 1B enzyme (FIGS. 2A and 2B, respectively) were minimized by an ab initio method using a 3-21G basis set on a CONVEX mainframe computer using GAUSSIAN 92 (GAUSSIAN 92, Gaussian, Inc., Carnegie Office Park, Building 6, Pittsburgh, Pa. 15106). The geometry of the binding site and mode of binding of the phosphonate were derived from X-ray crystallographic data of a difluorophosphonate-containing inhibitor bound within the PTP 1B catalytic site. During the minimization of the difluoromethylphosphonate-enzyme complex, the geometry of the binding site was fixed relative to the X-ray structure, and the geometry parameters and position of the phosphonate were optimized. FIGS. 2A and 2B set forth the energy minimized structures of $HCF_2PO$ (O—)$_2$ (FIG. 2A) and $CH_2(CO_2-)$, (FIG. 2B) bound within the protein tyrosine phosphatase 1B (PTP-1B) catalytic site. The minimized geometry of the phosphonate is shown in FIG. 2A. In minimizing the complex of the PTP 1B with the malonate structure not only the geometry parameters and position of the malonate were optimized, but also the geometry of the enzyme structure within the binding site during the first 50 hours of CPU time. The minimized malonate complex is shown in FIG. 2B. The overall geometry of binding was based on the X-ray structure of an aryl difluorophosphonate inhibitor complexed to PTP-1B.

Example 3

Tissue Culture Cell Line

Either of the following cell lines which overexpress human insulin receptors may be used for the assay of insulin receptor dephosphorylation by recombinant PTP 1B:

(1) L6: rat skeletal muscle myoblasts (may be obtained from the ATCC under ATCC Accession No. CRL1458); and (2) HEPG2: human hepatocellular carcinoma (may be obtained from the ATCC under ATCC Accession No. HB8065).

The cells were maintained in F-12 medium containing 10% fetal bovine serum and were cultured to confluence.

Example 4

Preparation of Partially Purified Human Insulin Receptors

Membranes from the cultured cells, overexpressing human insulin receptors were isolated and solubilized with Triton X-100, essentially as described by Liotta et al. (Liotta, A. S., et al., *J. Biol. Chem.* 269:22996–23001 (1994)). In brief, cells were scraped off the dishes in an isotonic homogenization buffer that contained 10 mM HEPES, pH 7.5, 0.25M sucrose, 5 mM EDTA, 20 µg/ml aprotinin, 10 µg/ml leupeptin, 0.2 mM phenylmethylsulfonyfluoride (PMSF), and pelleted by centrifugation at 300×g for 10 minutes. The cell pellet was resuspended in homogenization buffer ($43 \times 10^6$ cells/ml) and homogenized twice using a Polytron homogenizer (Brinkman) at a setting of 7, for 15 seconds each time. The homogenate was centrifuged at 12,000×g for 20 minutes at 4° C., and the pellet containing nuclei, debris, and mitochondria was discarded. The supernatant was centrifuged at 100,000×g for 60 minutes at 4° C., and the resulting crude membrane pellets were washed and frozen at −70° C. When needed, the membrane pellet was resuspended in solubilization buffer containing 50 mM HEPES, pH 7.5, 0.25 M sucrose, 20 µg/ml aprotinin, 10 µg/ml leupeptin, 0.2 mM PMSF and 1% Triton X-100 (w/v) (3 to 5 mg protein/mL solubilization buffer.) After a 30 minute incubation on ice with occasional stirring, the mixture was centrifuged at 100,000×g for 60 minutes at 4° C., and the insoluble material discarded. Purified insulin receptors from solubilized membranes were obtained after passing through a wheat germ agglutin (WGA) (obtained from Vector Laboratories, Inc., Burlingame, Calif.) column following the method of Brillon et at. (Brillon, D.J., et al., *Endocrinology* 123:1837–1847 (1988). The WGA eluate that contained purified receptors was divided into 100 µl aliquots and stored −70° C.

Example 5

Assay of Insulin Receptor Dephosphorylation by Recombinant PTP 1B

WGA-purified human insulin receptors were autophosphorylated with [γ-$^{32}$P]ATP as previously described (Liotta, A.S., et al., *J. Biol. Chem.* 269:22996–23001 (1994)), and this $^{32}$P-labeled insulin receptor was used as substrate for the assay of PTP 1B activity, essentially following the method described by Burke et al. (Burke, T. R. Jr., *Biochem, Biophys. Res. Commun.* 204:129–134 (1994)). In brief, $^{32}$P-labeled autophosphorylated insulin receptors (10 µg/ml) were incubated with 0.5 µg/ml recombinant PTP 1B at 22° C. in a 100 µl reaction containing 50 mM HEPES, pH 7.5, 0.1 mg/ml BSA, 5 mM DTT, 5 mM EDTA, 0.05% Triton X-100, in the absence or presence of various peptides at the indicated concentrations. The assay was terminated at various intervals by transferring an aliquot of the reaction mixture to a tube that contained 1 volume of 2-fold concentrated Laemmli sample buffer (36); samples were heated at 95° C. for 5 minutes prior to electrophoresis in 7.5% SDS-polyacrylamide gels under reducing conditions. The $^{32}$P remaining in the 95 kDa insulin receptor β-subunit was quantified by Betagen counting of the fixed and dried gels.

Example 6

Preparation of monofluoro-OMT

Monofluoro-OMT (FOMT) (formula no. 13), a derivative of OMT, was prepared from formula no. 11 by electrophilic fluorination, yielding formula no. 12, which was then demethylated, yielding formula no. 13.

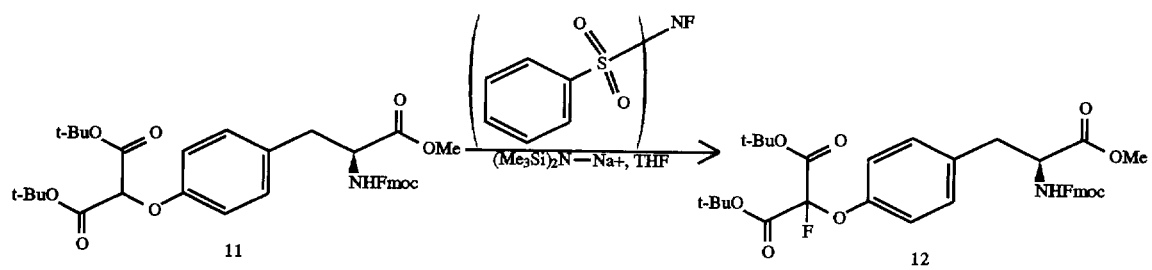

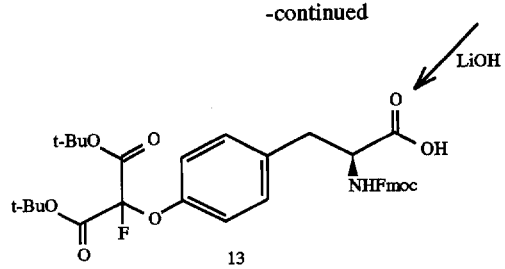

Example 7

The synthesis of 0,0-bis(tert-butyl)-N-Fmoc OMT (formula no. 5) is set forth in the schematic below using synthetic methodology previously reported. Starting from known (formula no. 9) reaction with diazo di-tertbutyl malonate (formula no. 10) in the presence of rhodium diacetate gave protected OMT derivative formula no. 11. Hydrolysis of the methyl ester provided the desired formula no. 5.

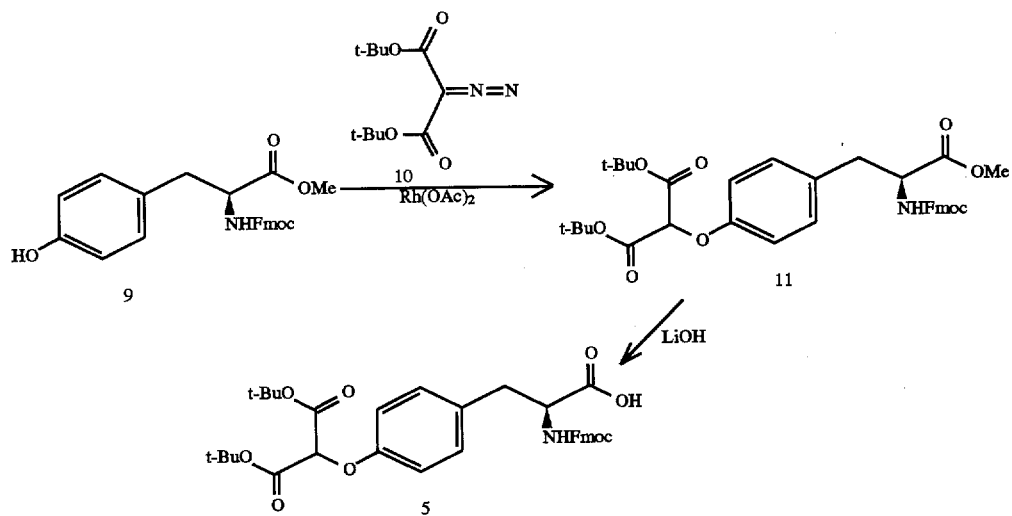

The n-butyl or alkyl diesters formula no. 6 can be prepared as above using the corresponding diazo di-(n-butyl) malonate (or dialkyl ester) and $N^\alpha$-fmoc tyrosinate tert-butyl ester, followed by treatment with TPA. Alternatively, compound 11 can be treated with acid (trifluoroacetic acid) to hydrolyze the tert-butyl groups, then re-esterified with the desired ester group. Selective hydrolysis of the OMe ester with LiOH would then provide final products of formula no. 6.

Example 8

Preparation of SH2 domain inhibitory peptides.

L-O-malonyltyrosine (L-OMT 4), a non-phosphorus containing pTyr mimetic, was incorporated into SH2 domain inhibitory peptides using solid-phase peptide techniques and the protected analogue (L)-$N^\alpha$-fmoc-O'-[(O",O"-(tert-butyl) malonyl]tyrosine (Ye, B. E. and Burke, T. R., Jr., Tetrahedron Lett. (in review)).

The sequences of these peptides are identical to pTyr and $F_2$Pmp containing peptides which were previously shown to exhibit high affinity to the desired SH2 domain constructs.

(See Burke, T. R., Jr., et al., Biochemistry 33:6490–6494 (1994); and Smyth, M. S., et al., Tetrahedron Lett. 33:4137–4140 (1992)).

A. Preparation of the peptide Ac-Asp-[L-OMT]-Val-Pro-Met-Leu-amide (SEQ. ID. NO. 1) against the PI-3 kinase C-terminal p85 SH2 domain.

The OMT-containing peptide exhibiting inhibitory potency against the SH2 domain was derived from Tyr751 of the PDGF receptor for inhibition of the PI3-kinase p85 C-terminal SH2 domain (See Piccione, E., et al., Biochemistry 32:3197–3202 (1993)), and synthesized by introducing the pTyr mimetic L-O-malonyl tyrosine (L-OMT) into the peptide Ac-Asp-[L-OMT]-Val-Pro-Met-Leu-amide by solid phase peptide techniques using the Di-tert-Butyl protected Fmoc-OMT. OMT.

Competition assays were performed to determine the relative SH2 domain affinities for the peptide vs. high affinity phosphopeptide ligands, as set forth in Example 9. Table 1 sets forth the inhibition constants of the peptide Ac-Asp-[L-OMT]-Val-Pro-Met-Leu-amide (peptide no. 6) against the pI-3 kinase C-terminal p85 SH2 domain construct. Also shown in Table 1 are the inhibition constants of identical peptides having either pTyr or L-$F^2$Pmp substituted in place of the L-OMT moiety.

B. Preparation of the peptide Ac-Gln-[L-OMT]-Glu-Glu-Ile-Pro-amide (SEQ. ID. NO. 2) against the Src SH2 domain.

The peptide Ac-Gln-[L-OMT]-X-Glu-Glu-Ile-Pro-amide was derived from Tyr324 of the hamster polyoma virus middle T antigen for inhibition of the Src SH2 domain (See Payne, G., et al., Proc. Natl. Acad. Sci. USA 90:4902–4906 (1993); and Songyang, Z., et al., Cell 72:767–778 (1993)).

Competition assays were performed to determine the relative SH2 domain affinities for the peptide vs. high affinity phosphopeptide ligands, as set forth in Example 9. Table 1 sets forth the inhibition constants of the peptide Ac-Gln-[L-OMT]-Glu-Glu-Ile-Pro-amide (peptide no. 7) against the Src SH2 domain construct. Also shown in Table 1 are the inhibition constants of identical peptides having either pTyr or L-F$^2$Pmp-substututed in place of the L-OMT moiety.

C. Preparation of the peptide Ac-Asn-[L-OMT]-Val-Asn-Ile-Glu-amide (SEQ. ID. NO. 3) against the Grb2 SH2 domain.

The peptide Ac-Asn-[L-OMT]-Val-Asn-Ile-Glu-amide was derived from Tyr895 of IRS-1 for inhibition of the Grb2 SH2 domain (See Sun, S. J., et al., *Mol. Cell. Biol.* 13:7428–7428 (1993)). Competition assays were performed to determine the relative SH2 domain affinities for the peptide vs. high affinity phosphopeptide ligands, as set forth in Example 9. Table 1 sets forth the inhibition constants of the peptide Ac-Asn-[L-OMT]-Vai-Asn-Ile-Glu-amide (peptide no. 8) against the Grb2 SH2 domain construct. Also shown in Table 1 are the inhibition constants of identical peptides having either pTyr or L-F$^2$Pmp substituted in place of the L-OMT moiety.

D. Preparation of the peptide Ac-Leu-Asn-[L-OMT]-Ile-Asp-Leu-Asp-Leu-Val-amide (SEQ. ID. NO. 4) against the SH-PTP2 SH2 domain.

The peptide Ac-Leu-Asn-[L-OMT]-Ile-Asp-Leu-Asp-Leu-Val-amide was derived from Tyr1172 of IRS-1 for inhibition of the SH-PTP2 (also known as Syp) N-terminal SH2 domain (See Sun, S. J., et al., *Mol. Cell. Biol.* 13:7428–7428 (1993)). Competition assays were performed to determine the relative SH2 domain affinities for the peptide rs. high affinity phosphopeptide ligands, as set forth in Example 9. Table 1 sets forth the inhibition constants of the peptide Ac-Leu-Asn-[L-OMT]-Ile-Asp-Leu-Asp-Val-amide (peptide no. 9) against the SH-PTP2 SH2 domain construct. Also shown in Table 1 are the inhibition constants of identical peptides having either pTyr or L-F$^2$Pmp substituted in place of the L-OMT moiety.

TABLE 1

Inhibition Constants of Peptide Inhibitors

| | | IC50 ± S.E. | | |
|---|---|---|---|---|
| No. | Peptide | SH2 Domain | X = pTyr* | L-F2Pmp* | L-OMT |
| 6 | Ac-D-X-V-P-M-L-amide | p85 (C-terminal) | 0.15 ± 0.03 | 0.17 ± 0.02 | 14.2 ± 1.3 |
| 7 | Ac-Q-X-E-E-I-P-amide | Src | 5.7 ± 0.7 | 1.0 ± 0.2 | >200 |
| 8 | Ac-N-X-V-N-I-E-amide | Grb2 | 0.9 ± 0.1 | 4.7 ± 0.7 | >600 |
| 10 | Ac-L-N-X-I-D-L-D-L-V-amide | SH-PTP2 (N-teminal) | 4$^b$ | 23$^b$ | 22.0 ± 1.4 |

*Except where indicated, inhibition constants have previously been reported. (See Burke, et al., Biochemistry 33:6490–6494 (1994)).
$^b$Previously reported. (See Xiao, S., et al., J. Biol. Chem. 269:21244–21248 (1994)).

Example 9

SH2 Domain Binding Assays

Details of the 3H2 domain competition assay are described by Piccione, E., et al., *Biochemistry* 32:3197–3202 (1993). Briefly, four distinct assays were used to determine relative SH2 domain affinities for pTyr analogues vs. high affinity phosphopeptide ligands. In each assay a glutathione S-transferase (GST)/SH2 domain fusion protein was paired with an appropriate high-affinity [$^{125}$I] Bolton-Hunter radiolabeled phosphopeptide, and varying concentrations of unlabeled peptides were added as competitors. The C-terminal SH2 domain of PI 3-kinase p85 was paired with IRS-1pY628, GNGDpYMPMSPK (SEQ ID NO. 5) (See Piccione, E., et al., *Biochemistry* 32:3197–3202 (1993)), the Src SH2 domain was paired with hmt pY324, KEPQpYEEIPIYL (SEQ ID NO. 6) (See Payne, G., et al., *Proc. Natl. Acad. Sci. USA* 90:4902–4906 (1993), the PLCγ-C SH2 domain was paired with PDGF pY1021, DNDpYIIPLPDPK (SEQ ID NO. 7) (See Piccione, E., et al., *Biochemistry* 32:3197–3202 (1993)), and the Lck SH2 domain was paired with the hmTpY324 sequence similar to assays conducted on the Src SH2 domain. An underline denotes the position of the [$^{125}$I]Bolton-Hunter modified lysine. GST/SH2 domain fusion proteins (0.5–1.0 μM, estimated by Bradford assay), 35 fmol of HPLC-purified, [$^{125}$I] Bolton-Hunter-treated phosphopeptide (67 nCi), and varying concentrations of pTyr analogues were combined in 200 μl total volume of 20 mM Tris-HCl, 250 mM NaCl, 0.1% bovine serum albumin, 10 mM dithiothreitol, pH 7.4, and vortexed. Glutathione-agarose (25 μl of a 1:4 aqueous slurry, Molecular Probes) was added and the samples were incubated overnight at 22° C. with constant mixing. Following centrifugation for 5 min at 12,000 g, supernatant solutions were removed by aspiration and [$^{125}$I]radioactivity associated with the unwashed pellets was determined with a γ-counter.

Example 10

Molecular Modeling Studies

Figure 1A:
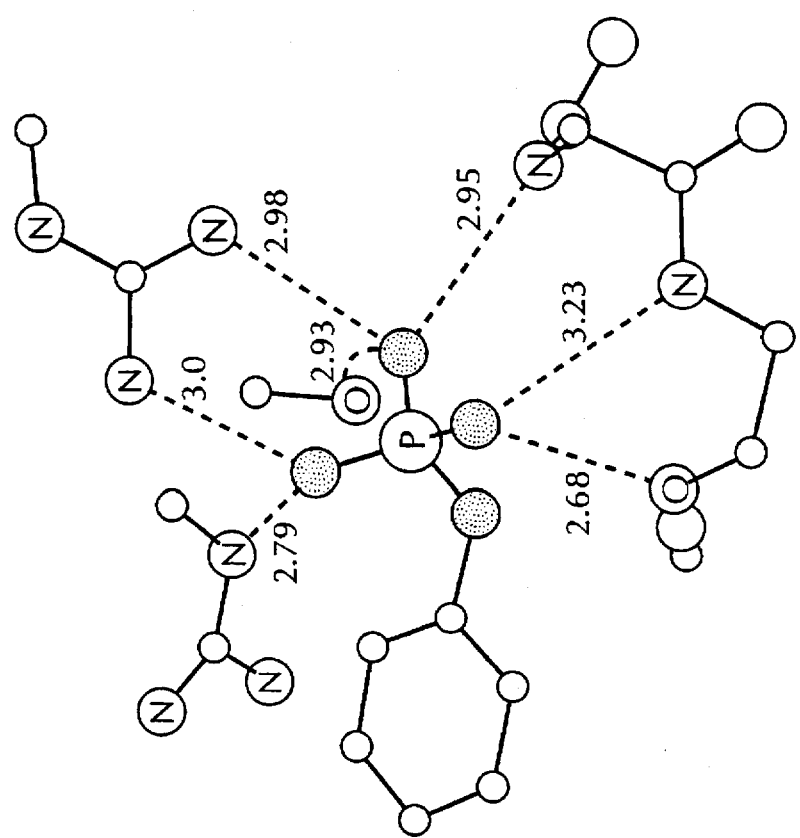

In order to compare the SH2 domain interaction of the OMT residue of the present invention with that of a native pTyr pharmacophore, molecular modeling studies were conducted using a previously reported X-ray structure of a high affinity pTyr peptide bound to the p56$^{lck}$ SH2 domain. FIGS. 1A and 1B set forth the structures and relative binding sites of (A) arylphosphate and (B) arylmalonate pharmacophores to the p56$^{lck}$ SH2 domain. Complexation of the pTyr phenyl phosphate pharmacophore within this SH2 domain is shown in FIG. 1A. Binding of the corresponding OMT pharmacophore is shown in FIG. 1B. The phosphate and malonate oxygen atoms are shaded. The structure of FIG. 1A shows complexation of the pTyr phenyl phosphate pharmacophore within the SH2 domain, and was derived from the previously reported X-ray structure of a bound high affinity pTyr-peptide (See Eck, M. J., et al. *Nature* 362:87–91 (1993)), while the structure of FIG. 1B, which shows binding of the corresponding OMT pharmacophore, was obtained by molecular modeling as herein described. Although the phosphate and malonate structures are chemically quite different, and the malonate group occupies approximately 18 % more volume than the phosphate, their interactions with the SH2 domain are remarkably similar, and both structures can be accommodated while maintaining nearly identical SH2 domain geometries.

Example 11

Preparation of the peptide Ac-D-A-D-E-OMT-L-amide (SEQ. ID. NO. 8) and testing against PTB-1B.

The peptide Ac-D-A-D-E-OMT-L-amide (SEQ. ID. NO. 8) was prepared by solid-phase peptide techniques using the Di-tert-butyl protected Fmoc-OMT 2.

The peptide Ac-D-A-D-E-OMT-L-amide (SEQ. ID. NO. 8) was then examined for inhibitor potency against PTB-1B dephosphorylation of phosphorylated insulin receptor.

Briefly, this assay was conducted as follows: $^{32}$P-labeled autophosphorylated insulin receptors were incubated with recombinant PTP-1B in the absence or the presence of Ac-D-A-D-E-OMT-L-amide (SEQ. ID. NO. 8) at various concentrations. The assay was terminated at different intervals and examined by electrophoresis in 7.5 % SDS-polyacrylamide gels under reducing conditions. The $^{32}$P remaining in the 95 kDa insulin receptor β-subunit was quantified by Betagen counting of the fixed and dried gels. Under identical conditions, the F$_2$Pmp-containing peptide and the Pmp-containing peptide showed inhibition constants of 100 nM and 200 µM, respectively. (See Burke, et al., *Biochem. Biophys. Res. Commun.* 204:129–134 (1994)). The peptide Ac-D-A-D-E-OMT-L-amide (SEQ. ID. NO. 8) exhibited an inhibition constant of approximately 10 µM.

Figure 3:
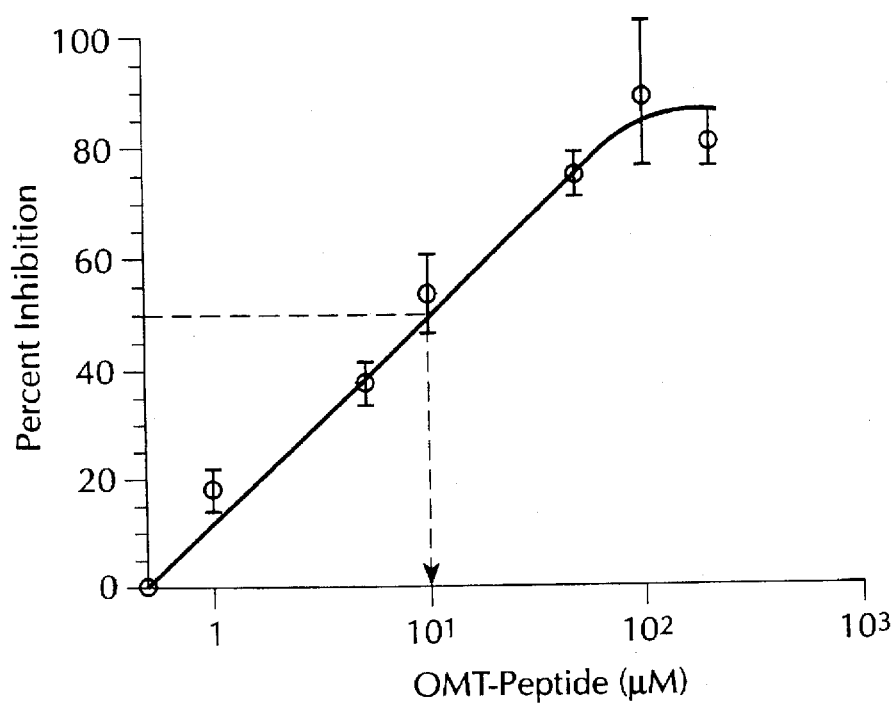
FIG. 3.

The effect of the OMT-peptide Ac-D-A-D-E-[L-OMT]-L-amide (SEQ. ID. NO. 8) on PTP 1B catalyzed insulin receptor dephosphorylation using $^{32}$P-labeled intact insulin receptor as substrate is set forth in FIG. 3.

Figure 4:
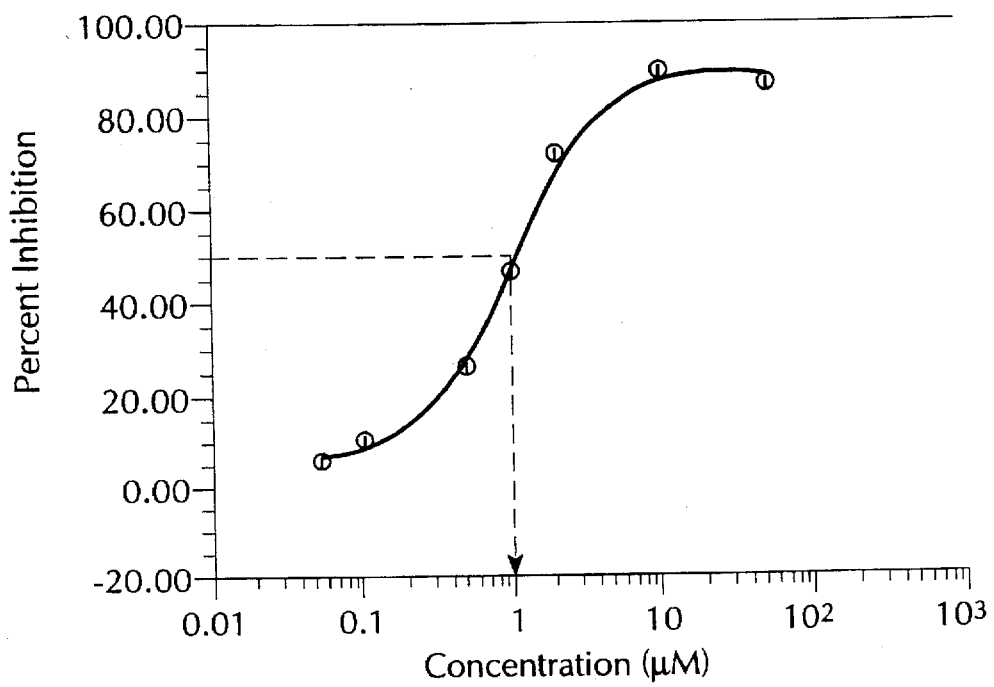
FIG. 4.

A similar set of experiments was performed using the peptide Ac-D-A-D-E-9L-FMOT)-L-amide (SEQ. ID. NO. 8). An IC$_{50}$ value of 1 µM was obtained, demonstrated graphically in FIG. 4.

REFERENCES

1. Albericio, F., Kneib-Cordonier, N., Bianacalana, S., Gera, L., Masada, R. I., Hudson D. and Barany, G. (199)) J. Org. Chem. 55, 3730–3743.
2. Barford, D., Flint, A. J. and Tonks, N. K. (1994) Science 263, 1397–1404.
3. Berggren, M. M.; Burns, L.A.; Abraham, R. T.; Powis, G. Inhibition of Protein Tyrosine Phosphatase by the Antitumor Agent Gallium Nitrate. Cancer Res 1993, 53, 1862–1866.
4. Blackburn, G. M. Phosphonates as analogues of biological phosphates. Chem. Ind. (London)1981, 134–138.
5. Brillon, D. J., Henry, R.r., Klein, H. H., Olefsky, J. M. and Freideberg, g.R. (1988).
6. Brugge, J. S. New intracellular targets for therapeutic drug design. Science 1993, 260, 918–919.
7. Brunton, V. G.; Workman, P. Cell-Signaling Targets for Antitumor Drug Development. Cancer Chemother Pharmacal 1993, 32, 1–19.
8. Burke, T.R., Jr. Protein-tyrosine kinase inhibitors. Drugs of the Future 1992, 17, 119–131.
9. Burke, T. R., Jr.; Kole, H. K.; Roller, P. P. Potent inhibition of insulin receptor dephosphorylation by a hexamer peptide containing the phosphotyrosyl mimetic F2Pmp. Biochem. Biophys. Res. Commun. 1994, 204, 129–134.
10. Burke, T. R., Jr.; Lim, B. B. Phosphonoalkyl phenylalanine compounds suitably protected for use in peptide synthesis. U.S. Pat. No. 5,200,546 Apr. 16, 1993 (Appl. Sep. 30, 1991) 1993,
11. Burke, T. R., Jr.; Nomizu, M.; Otaka, A.; Smyth, M. S.; Roller, P. P.; Case, R. D.; Wolf, G.; Shoelson, S. E. Cyclic peptide inhibitors of phosphatidylinositol 3-kinase p85 SH2 domain binding Biochem. Biophys. Res. Commun. 1994, 201, 1148–1153.
12. Burke, T. R., Jr.; Russ, P.; Lim, B. (1991) Synthesis 11, 1019–1020.
13. Burke, T.R., Jr.; Russ, P.; Lim, B. Preparation of 4-[bis (tert-butyl)phosphonomethyl]-N-Fmoc-DL-phenylalanine; a hydrolyrically stable analogue of O-phosphotyrosine potentially suitable for peptide synthesis. Synthesis 1991.11, 1019–1020.
14. Burke, T. R., Jr.; Smyth, M.; Nomizu, M.; Otaka, A.; Roller, P. P. Preparation of fluoro- and hydroxy-4-phosphonomethyl-D,L-phenylalanine suitably protected for solid-phase synthesis of peptides containing hydrolyrically stable analogues of O-phosphotyrosine. J. Org. Chem. 1993, 58, 1336–1340.
15. Burke, T. R., Jr.; Smyth, M.; Nomizu, M.; Otaka, A.; Roller, P. O. (1993) J. Org. Chem. 58, 1336–1340.
16. Burke, T. R., Jr.; Smyth, M. S.; Otaka, A.; Nomizu, M.; Roller, P. P.; Wolf, G.; Case, R.; Shoelson, S. E. Nonhydrolyzable phosphotyrosyl mimetics for the preparation of phosphatase-resistant SH2 domain inhibitors. Biochemistry 1994, 33, 6490–6494.
17. A preliminary disclosure of this work has appeared: Burke, T. R., Jr., Ye., B., Akamatsu, M., Yan, X., Kole, H. K., Wolf, G., Shoelson, S. E. and Roller, P. O. 209th National American Chemical Society Meeting, Anaheim, Calif. (1995) MEDI 14.
18. Burke, T. R.; Kole, H. K.; Roller, P. O. (1994) Biochem: Biophys. Res. Commun. 204, 129–134.
19. Burke, T. R.; Smyth, M. S.; Otaka, A.; Roller, P. O. (1993) Tetrahedron Lett. 34, 4125–4128.
20. Burke, T. R.; Smyth, M. S.; Otaka, A.; Roller, P. P. Synthesis of 4-Phosphono(Difluoromethyl)-D, L- Phenylalanine and N-Boc and N-Fmoc Derivatives Suitably Protected for Solid-Phase Synthesis of Nonhydrolyzable Phosphotyrosyl Peptide Analogues. Tetrahedron Lett. 1993, 34, 4125–4128.
21. Cantley, L. C.; Auger, K. R.; Carpenter, C.; Duckworth, B.; Granziani, A.; Kapeller, R.; Soltoff, S. Oncogenes and signal transduction. Cell 1991, 64, 281–302.
22. Chatterice, S.; Goldstein, B. J., Csermerly, P.; Shoelson, S. E. Phosphopeptide substrates and phosphonopeptide inhibitors of protein-tyrosine phosphatases, in Peptides: Chemistry and Biology, J. E. Rivier and J. A. Smith, Editor. 1992, Escom Science Publishers: Leiden, Netherland, p. 553–555.
23. Corey, S. D.; Pansegrau, P. D.; Walker, M. C.; Sikorski, J. A. EPSP synthase inhibitor design III. Synthesis & evaluation of a new 5-oxaminic acid analog of EPSP which incorporates a malonate ether as a 3-phosphate mimic. Bioorg. Med. Chem. Lett. 1993, 3, 2857–2862.
24. Diamond, R. H., Cressman, D. E., Lax, T. M., Abrams, C. S. and Taub, R. (1994) Mol. Cell. Biol. 14, 3752–3762.
25. Domchek, S. M.; Auger, K. R.; Chatterjee, S.; Burke, T. R.; Shoelson, S. E. Inhibition of SH2 Domain/Phosphoprotein Association by a Nonhydrolyzable Phosphonopeptide. Biochemistry 1992, 31, 9865–9870.
26. Engel, R. Phosphonic acids and phosphonates as antimetabolites, in the role of phosphonates in living systems. R. L. Hilderbrand, Editor. 1983, CRC Press, Inc: Boca Raton, Fla. p. 97–138.
27. Errasfa, M.; Stem, A. Inhibition of protein tyrosine phosphatase activity in HER14 cells by melittin and Ca2+ ionophore A23187. Eru J. Pharmacal .1993, 247, 73–80.
28. Fantl, W. J.; Escobedo, J. A.; Martin, G. A.; Turck, C. W.; Delrosario, M.; Mccormick, F.; Williams, L. T. Distinct phosphotyrosines on a growth factor receptor bind to specific molecules that mediate different signaling pathways. Cell 1992, 69, 413423.
29. Fantl, W. J.; Johnson, D. E.; Williams, L. T. Signaling by Receptor Tyrosine Kinases. Annu Rev Biochem 1993, 453481.
30. Farquhar, D., Chen, R. and Khan, S. (1995) J. Med. Chem. 38, 488–495.
31. Freeman, S., Irwin, W. J., Mitchell, A. G., Nicholls, D. and Thomson, W. (1991) J. Chem. Soc. Chem. Commun. 875–877.
32. Freeman, S.; Irwin, W. J.; Mitchell, A. G.; Nicholls, D.; Thomson, W. Bioreversible protection for the phospho group: Chemical stability and bioactivation of di(4-acetoxybenzyl) methylphosphonate with carboxyesterase. J. Chem. Soc. Chem. Commun. 1991, 875–877.

33. Fry, M. J.; Panayotou, G.; Booker, G. W.; Waterfield, M. D. New Insights into Protein-Tyrosine Kinase Receptor Signaling Complexes. Protein Sci. 1993, 2, 1785–1797.

34. GAUSSIAN 92, Gaussian, Inc., Carnegie Office Park, Building 6, Pittsburgh, Pa. 15106.

35. Ghosh, J.; Miller, R. A. Suramin, an experimental chemotherapeutic drug, irreversibly blocks T cell CD45-protein tyrosine phosphatase in vitro. Biochem Biophys Res Commun 1993, 194, 36–44.

36. Igarashi, K., David, M., Larner, A. C. and Finbloom, D. S. (1993) Mol. Cell., Biol. 13, 3984–3989.

37. Igarashi, K.; David, M.; Larner, A. C.; Finbloom, D. S. Invitro Activation of a Transcription Factor by Gamma Interferon Requires a Membrane-Associated Tyrosine Kinase and Is Mimicked by Vanadate. Mol Cell Biol 1993, 13, 3984–3989.

38. Imoto, M.; Kekeya, H.; Sawa, T.; Hayashi, C.; Hamada, M.; Takeuchi, T.; Umezawa, K. Dephostatin, A Novel Protein Tyrosine Phosphatase Inhibitor Produced by Streptomyces .1. Taxonomy, Isolation, and Characterization, J. Antibiot 1993, 46, 1342–1346.

39. Iyer, R. P.; Phillips, L. R.; Biddle, J. A.; Thakker, D. R.; Egan, W.; Aoki, S.; Mitsuya, H. Synthesis of Acyloxyalkyl Acylphosphonates As Potential Prodrugs of the Antiviral, Trisodium Phosphonoformate (Foscamet Sodium). Tetrahedron Letters 1989, 30, 7141–7144.

40. Koretzky, G. A. (1993)FASEB J. 7, 420–426.

41. Koretzky, G. A. Role of the CD45 Tyrosine Phosphatase in Signal Transduction in the Immune System. Faseb J. 1993, 7, 420–426.

42. Kusari, J., Kenner, K. A., Suh, K. I., Hill, D. E. and Henry, R. R. (1994) J. Clin. Invest. 93, 1156–1162.

43. Liotta, A. S., Kole, H. K., Fales, H. M., Roth, L. and Bernier, M. (1994) J. Biol. Chem. 269, 22996–23001.

44. Lombaert, S. D., Erion, M. D., Tan, 1., Blanchard, L., El -Chehabi, L., Ghari, R. D., Sakane, Y., Berry, C. and Trapani, A. J. (1994) J. Med. Chem. 37, 498–511.

45. Lombaert, S. D.; Erion, M. D., Tan. J.; Blanchard, L.; El-Chehabi, L.; Ghai, R. D.; Sakane, Y.; Berry, C.; Trapani, A. J. N-Phosphonomethyl dipeptides and their phosphonate prodrugs, a new generation of neutral endopeptidase (NEP, EC 3.4.24.11). J. Med. Chem. 1994, 37, 498–511.

46. Margolis, B. Proteins with SH2 Domains—Transducers in the Tyrosine Kinase Signaling Pathway. Cell. Growth Differ. 1992, 3, 73–80.

47. Marzabadi, M. R.; Font, J. L.; Gruys, K. J.; Pansegrau, P. D.; Sikorski, J. A. Design & synthesis of a novel EPSP synthase inhibitor based on its ternary complex with shikimate-3-phosphate and glyphosphate. Bioorg. Med. Chem. Lett. 1992, 2, 1435–40.

48. McGuigan, C., Pathirana, R. N., Mahmood, N. and Hay, A. J. (1992) Bioorg. Med. Chem. Lett. 2, 701–704.

49. Miller, M. J.; Anderson, K. S.; Braccolino, D. S.; Cleary, D. G.; Gruys, K. J.; Han, C. Y.; Lin, K. C.; Pansegrau, P. D.; Ream, J. E.; Sikorski, R. D. S. J. A. EPSP synthase inhibitor design II. The importance of the 3-phosphate group for ligand binding at the shikimate-3-phosphate site & the identification of 3-malonate ethers as novel 3-phosphate mimetics. Bioorg. Med. Chem. Lett. 1993, 7, 1435–1440.

50. For a lead reference see: Miller, M. J., Braccolino, D. S., Cleary, D. G., Ream, J. e., Walker, M. C. and Sikorski, J. A. (1994) Bioorg. Med. Chem. Lett. 4, 2605–2608.

51. Miresluis, A. R.; Thorpe, R. (1991) J. Biol. Chem. 266, 18113–188118.

52. Miresluis, A. R.; . Thorpe, R. Interleukin-4 Proliferative Signal Transduction Involves the Activation of a Tyrosine-Specific Phosphatase and the Dephosphorylation of an 80-kDa Protein. J Biol Chem 1991, 266, 18113–18118.

53. Mitchell, A. G.; Thomson, W.; Nicholls, D.; Irwin, W. J.; Freeman, S. Bioreversible protection for the phospho group: Bioactivation of the di(4-acyloxybenzyl) and mono(4-diacyloxybenzyl) phosphoesters of methylphosponate and phosphonoacetate. J. Chem. Soc. Perkin Trans. I 1992.

54. Morla, A. O., Beach, G. and Wang, J. Y. J. (1989) Cell 58, 193–203.

55. Morla, A. O.; Beach, G.; Wang, J. Y. J. Reversible tyrosine phosphorylation of cdc2:dephosphorylation accompanies activation during entry into mitosis. Cell 1989, 58, 193–203.

56. Nomizu, M.; Otaka, A.; Burke, T. R.; Roller, P. P. Synthesis of Phosphonomethyl-Phenylalanine and Phosphotyrosine Containing Cyclic Peptides as Inhibitors of Protein Tyrosine Kinase/Sh2 Interactions. Tetrahedron 1994, 50, 2691–2702.

57. Nomizu, M.; Otaka, A.; Smyth, M. S.; Shoelson, S. E.; Case, R. D.; Burke, T. R., Jr.; Roller, P. P. Synthesis and structure of SH2 binding peptides containing 4-phosphonomethyl-phenylalanine and analogs in Peptide Chemistry: Proceedings of the 31st Japanese symposium 1994. Kobe: Protein Research Foundation, Osaka, Japan.

58. Otaka, A.; Burke, T. R., Jr.; Smyth, M. S.; Nomizu, M.; Roller, P. P. Deprotection and cleavage methods for protected peptide resins containing 4-[ (diethylphosphono) difluoromethyl]-D,L-phenylalanine residues. Tetrahedron Lett. 1993, 34, 7039–7042.

59. Otaka, A.; Nomizu, M.; Smyth, M. S.; Case, R. D.; Shoelson, S. E.; T. R. Burke, J.; Roller, P. P. Synthesis and structure-activity studies of SH2 binding peptides containing hydrolytically stable analogs of O-phosphotyrosine. in Peptides: Chemistry and Biology: Proceedings of the Thirteenth American Peptide Symposium 1993. Edmonton, Alberta, Canada: ESCOM Publishers, Leiden, The Netherlands.

60. Panayotou, G.; Waterfield, M. D. The Assembly of Signaling Complexes by Receptor Tyrosine Kinases. Bioessays 1993, 15, 171–177.

61. Pawson, T.; Gish, G. D. SH2 and SH3 Domains—From Structure to Function. Cell 1992, 71,359–362.

62. Pawson, T.; Schlessinger, J. SH2 and SH3 Domains. Curr Biol 1993, 3, 434–442.

63. Perigaud, C., Gosselin, G., Lefebvre, I., Girardet, J. L., Benzaria, S., Barber, I. and Imbach, J. L. (1993) Bioorg. Med. Chem. Lett 3, 2521–2526.

64. Piccione, E.; Case, R. D.; Domchek, S. M.; Hu, P.; Chaudhuri, M.; Backer, J. M.; Schlessinger, J.; Shoelson, S. E. Phosphatidylinositol 3-Kinase Kinase p85 SH2 Domain Specificity Defined by Direct Phosphopeptide/ SH2 Domain Binding. Biochemistry 1993, 32, 3197–3202.

65. Posner, B. I.; Faure, R.; Burgess, J. W.; Bevan, A. P.; Lachance, D.; Zhangsun, G. Y.; Fantus, I. G.; Ng, J. B.; Hall, D. A.; Lure, B. S.; Shaver, A.; Peroxovanadium Compounds—A New Class of Potent Phosphotyrosine Phosphatase Inhibitors Which Are Insulin Mimetics. J Biol Chem 1994, 269, 4596–4604.

66. Roller, P. P.; Otaka, A.; Nomizu, M.; Smyth, M. S.; Barchi, J. J., Jr.; Burke, T. R., Jr.; Case, R. D.; Wolf, G.;

Shoelson, S. E. Norleucine as a replacement for methionine in phosphatase-resistant linear and cyclic peptides which bind to p85 SH2 domains. Bioorg. Med. Chem. Lett. 1994, 1879–1882.

67. Sale, G. J. Insulin Receptor Phosphotyrosyl Protein Phosphatases and the Regulation of Insulin Receptor Tyrosine Kinase Action. Advances in Protein Phosphatases 1991, 6, 159–186.

68. Shoelson, S. E.; Chatterjee, S.; Chaudhuri, M.; Burke, T. R. Solid-phase synthesis of nonhydrolyzable phosphotyrosyl peptide analogues with N(alpha)-fmoc-(O,O-di-tert-butyl)phosphono-para-methylphenylalanine. Tetrahedron Lett. 1991, 32, 6061–6064.

69. Sikorski, J. A.; Miller, M. J.; Braccolino, D. S.; Clearly, D. G.; Corey, S. D.; Font, J. L.; Gruys, K. J.; Han, C. Y.; Lin, K. C.; EPSP synthase: the design and synthesis of bisubstrate inhibitors incorporating novel-3-phosphate phosphate mimics. Phosphorus, Sulfur Silicon Relat. Elem. 1993, 76, 115–118.

70. Smyth, M. S. and Burke, T. R., Jr. (1994) Tetrahedron Lett. 35, 551–554.

71. Smyth, M. S. Ford, H., Jr., and Burke, T. R., Jr (1992) Tetrahedron Lett. 33, 4137–4140.

72. Smyth, M. S.; Burke, T. R., Jr. Enantioselective synthesis of N-Boc and N-Fmoc protected diethyl 4-phosphonodifluoromethyl-L-phenylalanine; agents suitable for the solid-phase synthesis of peptides containing nonhydrolyzable analogues of O-phosphotyrosine. Tetrahedron Lett. 1994, 35, 551–554.

73. Smyth, M. S.; Ford, H., Jr.; Burke, T. R., Jr. A general method for the preparation of benzylic alpha, alpha-difluorophosphonic acids; non-hydrolyzable mimetics of phosphotyrosine. Tetrahedron Lett. 1992, 33, 4137–4140.

74. Songyang, Z.; Shoelson, S. E.; Chaudhuri, M.; Gish, G.; Pawson, T.; Haser, W. G.; King, F.; Roberts, T.; Ratnofsky, S.; Lechleider, R. J.; Neel, B. G.; Birge, R. B.; Fajardo, J. E.; Chou, M. M.; Hanafusa, H.; Schaffhausen, B.; Cantley, L. C. SH2 Domains Recognize Specific Phosphopeptide Sequences. Cell 1993, 72, 767–778.

75. Srivastva, D. N. and Farquhar, D. (1984) Bioorganic Chemistry 12, 118–129.

76. Srivastva, D. N.; Farquhar, D. Bioreversible phosphate protective groups: Synthesis and stability of model acyloxymethyl phosphates. Bioorganic chemistry 1984, 12, 118–129.

77. Tan, Y. H. (1993) Science 262, 376–377.

78. Tan, Y. H. Yin and Yang of Phosphorylation in Cytokine Signaling. Science 1993, 262, 376–377.

79. Walton, K. J. and Dixon, J. E. (1993) J. Biol. Chem. 62, 101–120.

80. Walton, K. M.; Dixon, J. E. Protein tyrosine phosphates. Ann. Rev. Biochem. 1993, 62, 101–120.

81. Wang, Q. P., Dechert, U.; Jirik, F.; Withers, S. G. Suicide Inactivation of Human Prostatic Acid Phosphatase and a Phosphotyrosine Phosphatase. Biochem Biophys Res Commun 1994, 200, 577–583.

82. Wange, R. L., Isakov, N., Burke, T. R., Jr., Otaka, A., Roller, P. O., Watts, J.D., Aebersold, R. and Samelson, L.W. (1995) J. Biol. Chem. 270, 944–948.

83. Watanabe, H.; Nakai, M.; Komazawa, K.; Sakurai, H. A new orally active insulin-mimetic vanadyl complex: vis (pyrrolidine-N-carbothioatao)oxovanadium (IV). J. Med. Chem. 1994, 37, 876–877.

84. Wiener, J. R., Hurteau, J. A., Kerns, B. J., Whitaker, R. S., Conaway, M. R., Berchuck, A. and Bast, R. C., Jr. (1994) Am. J. Obstet. Gynecol. 170, 1177–1183.

85. Wiener, J. R., Kerns, B., Harvey, E. L., Conaway, M. R., Iglehart, J. D., Betchuck, A. and Bast, R. C. (1994) J. Nat. Cancer Inst. 86, 372–378.

86. Xiao, S.; Rose, D. W.; Sasaoka, T.; Maegawa, H.; Burke, T. R.; Roller, P. P.; Shoelson, S. E.; Olefsky, J. M. Syp (SH-PTP2) is a positive mediator of growth factor-stimulated mitogenic signal transduction. J Biol Chem 1994, 269, 21244–21248.

87. Ye, B., Akamatsu, M., Yan, X., Wolf, G., Shoelson, S. E. and Roller P. O. and Burke, T. R., Jr. (in review) J. Med. Chem.

88. Ye, B. and Burke, T. R., Jr (in review) Tetrahedron Lett.

89. Zanke, B., Squire, J., Griesser, H., Henry, M., Suzuki, H., Patterson, B., Minden, M. and Mak, T. W. (1994) Leukemia 8, 236–244.

90. Zhang, Z. Y.; Maclean, D.; McNamara, D. J.; Sawyer, T. K; Dixon, J. E. Protein Tyrosine Phosphatase Substrate Specificity—Size and Phosphotyrosine Positioning Requirements in Peptide Substrates. Biochemistry 1994, 33, 2285–2290.

91. Zheng, X. M.; Wang, Y.; Pallen, C. J. Cell Transformation and Activation of pp60(c-src) by Overexpression of a Protein Tyrosine Phosphatase. Nature 1992, 359, 336–339.

---

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
      ( A ) LENGTH: 6
      ( B ) TYPE: AMINO ACID
      ( C ) STRANDEDNESS: UNKNOWN
      ( D ) TOPOLOGY: UNKNOWN ( i x ) FEATURE:
      ( A ) NAME/KEY:
      ( B ) LOCATION:
      ( C ) IDENTIFICATION METHOD:
      ( D ) OTHER INFORMATION: Wherein Xaa is a residue of a unit derived from the O - malonyltyrosyl compounds of Formula II.

( x i ) SEQUENCE DESCRIPTION: SEQ ID NO: 1:

Asp Xaa Val Pro Met Leu
1               5

( 2 ) INFORMATION FOR SEQ ID NO:2:

( i ) SEQUENCE CHARACTERISTICS:
        ( A ) LENGTH: 6
        ( B ) TYPE: AMINO ACID
        ( C ) STRANDEDNESS: UNKNOWN
        ( D ) TOPOLOGY: UNKNOWN ( i x ) FEATURE:
        ( A ) NAME/KEY:
        ( B ) LOCATION:
        ( C ) IDENTIFICATION METHOD:
        ( D ) OTHER INFORMATION: Wherein Xaa is a residue
        of a unit derived from the O-malonyltyrosyl
        compounds of Formula II.

( x i ) SEQUENCE DESCRIPTION: SEQ ID NO: 2:

Gln Xaa Glu Glu Ile Pro
1               5

( 2 ) INFORMATION FOR SEQ ID NO:3:

( i ) SEQUENCE CHARACTERISTICS:
        ( A ) LENGTH: 6
        ( B ) TYPE: AMINO ACID
        ( C ) STRANDEDNESS: UNKNOWN
        ( D ) TOPOLOGY: UNKNOWN ( i x ) FEATURE:
        ( A ) NAME/KEY:
        ( B ) LOCATION:
        ( C ) IDENTIFICATION METHOD:
        ( D ) OTHER INFORMATION: Wherein Xaa is a residue
        of a unit derived from the O-malonyltyrosyl
        compounds of Formula II.

( x i ) SEQUENCE DESCRIPTION: SEQ ID NO: 3:

Asn Xaa Val Asn Ile Gln
1               5

( 2 ) INFORMATION FOR SEQ ID NO:4:

( i ) SEQUENCE CHARACTERISTICS:
        ( A ) LENGTH: 9
        ( B ) TYPE: AMINO ACID
        ( C ) STRANDEDNESS: UNKNOWN
        ( D ) TOPOLOGY: UNKNOWN ( i x ) FEATURE:
        ( A ) NAME/KEY:
        ( B ) LOCATION:
        ( C ) IDENTIFICATION METHOD:
        ( D ) OTHER INFORMATION: Wherein Xaa is a residue
        of a unit derived from the O-malonyltyrosyl
        compounds of Formula II.

( x i ) SEQUENCE DESCRIPTION: SEQ ID NO: 4:

Leu Asn Xaa Ile Asn Leu Asp Leu Val
1               5

( 2 ) INFORMATION FOR SEQ ID NO:5:

( i ) SEQUENCE CHARACTERISTICS:
        ( A ) LENGTH: 11
        ( B ) TYPE: AMINO ACID
        ( C ) STRANDEDNESS: UNKNOWN
        ( D ) TOPOLOGY: UNKNOWN ( i x ) FEATURE:
                    ( A ) NAME/KEY:
                    ( B ) LOCATION:
                    ( C ) IDENTIFICATION METHOD:
                    ( D ) OTHER INFORMATION: The C- terminal Lys is an
                            [ I125]Bolton-Hunter modified lysine.

( x i ) SEQUENCE DESCRIPTION: SEQ ID NO: 5:

Gly  Asn  Gly  Asp  Tyr  Met  Pro  Met  Ser  Pro  Lys
 1                    5                     10

( 2 ) INFORMATION FOR SEQ ID NO:6:

( i ) SEQUENCE CHARACTERISTICS:
                    ( A ) LENGTH: 12
                    ( B ) TYPE: AMINO ACID
                    ( C ) STRANDEDNESS: UNKNOWN
                    ( D ) TOPOLOGY: UNKNOWN ( i x ) FEATURE:
                    ( A ) NAME/KEY:
                    ( B ) LOCATION:
                    ( C ) IDENTIFICATION METHOD:
                    ( D ) OTHER INFORMATION: The N- terminal Lys is an
                            [ I125]Bolton-Hunter modified lysine.

( x i ) SEQUENCE DESCRIPTION: SEQ ID NO: 6:

Lys  Glu  Pro  Gln  Tyr  Glu  Glu  Ile  Pro  Ile  Tyr  Leu
 1                    5                     10

( 2 ) INFORMATION FOR SEQ ID NO:7:

( i ) SEQUENCE CHARACTERISTICS:
                    ( A ) LENGTH: 12
                    ( B ) TYPE: AMINO ACID
                    ( C ) STRANDEDNESS: UNKNOWN
                    ( D ) TOPOLOGY: UNKNOWN ( i x ) FEATURE:
                    ( A ) NAME/KEY:
                    ( B ) LOCATION:
                    ( C ) IDENTIFICATION METHOD:
                    ( D ) OTHER INFORMATION: The C- terminal Lys is an
                            [ I125]Bolton-Hunter modified lysine.

( x i ) SEQUENCE DESCRIPTION: SEQ ID NO: 7:

Asp  Asn  Asp  Tyr  Ile  Ile  Pro  Leu  Pro  Asp  Pro  Lys
 1                    5                     10

( 2 ) INFORMATION FOR SEQ ID NO:8:

( i ) SEQUENCE CHARACTERISTICS:
                    ( A ) LENGTH: 6
                    ( B ) TYPE: AMINO ACID
                    ( C ) STRANDEDNESS: UNKNOWN
                    ( D ) TOPOLOGY: UNKNOWN ( i x ) FEATURE:
                    ( A ) NAME/KEY:
                    ( B ) LOCATION:
                    ( C ) IDENTIFICATION METHOD:
                    ( D ) OTHER INFORMATION: Wherein Xaa is a residue
                            of a unit derived from the O-malonyltyrosyl
                            compounds of Formula II.

( x i ) SEQUENCE DESCRIPTION: SEQ ID NO: 8:

Asp  Ala  Asp  Glu  Xaa  Leu
 1                    5

What is claimed is:

1. O-malonyltryrosyl compounds of the Formula (I):

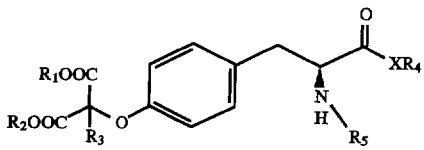 (I)

wherein $R_1$ and $R_2$ are independently hydrogen, optionally substituted alkyl, aralkyl, alkaryl, optionally substituted aryl, and optionally substituted heteroaryl;

wherein $R_3$ is hydrogen, halogen, amino, hydroxy, and alkoxy;

wherein X is nitrogen or oxygen;

wherein $R_4$ is hydrogen, optionally substituted alkyl, aralkyl, alkaryl, optionally substituted aryl, and optionally substituted heteroaryl;

wherein $R_5$ is hydrogen, fluorenyl methoxy carbonyl (FMOC), tert-butoxy carbonyl (BOC), and carbobenzoxy (CBZ), carbamoyl, optionally substituted alkyl, amido, optionally substituted aryl, and optionally substituted heteroaryl.

2. The O-malonyltryrosyl compound of Formula (I), claim 1, wherein $R_1$ and $R_2$ are independently tert-butyl, n-butyl, or hydrogen.

3. The O-malonyltryrosyl compound of Formula (I), claim 1, wherein $R_3$ is hydrogen or fluorine.

4. The O-malonyltryrosyl compound of Formula (I), claim 1, wherein $R_4$ is hydrogen, methyl, tert-butyl, or benzyl.

5. The O-malonyltryrosyl compound of Formula (I), claim 1, wherein $R_5$ is flurenyl methoxy carbonyl, tert-butoxy carbonyl, or carbobenzoxy.

6. A composition for affecting signal transduction pathways of cells, comprising at least one compound of Formula (I) of claim 1 in an amount effective to affect signal transduction pathways, and a suitable carrier.

7. O-malonyltryrosyl compounds of the Formula (II):

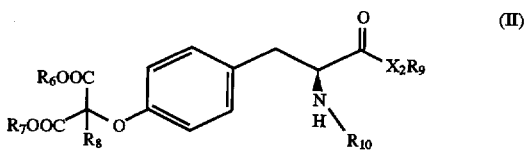 (II)

wherein $R_6$ and $R_7$ are independently hydrogen, optionally substituted alkyl, optionally substituted aryl, alkaryl, and ethhylenethioalkyl;

wherein $R_8$ is hydrogen, halogen, alkoxy, haloalkoxy, and substituted amino groups;

wherein $X_2$ is nitrogen or oxygen;

wherein $R_9$ is hydrogen, optionally substituted alkyl, aralkyl, alkaryl, optionally substituted aryl, and optionally substituted heteroaryl;

wherein $R_{10}$ is hydrogen, fluorenyl methoxy carbonyl (FMOC), tert-butoxy carbonyl (BOC), and carbobenzoxy (CBZ), carbamoyl, optionally substituted alkyl, amido, optionally substituted aryl, and optionally substituted heteroaryl; with the proviso that substituents of Formula (II) which can be substituted are optionally substituted.

8. O-malonyltryrosyl compounds of Formula (II) of claim 7 wherein $R_8$ is a halogen selected from the group consisting of fluorine, bromine or chlorine.

9. O-malonyltryrosyl compounds of Formula (II) of claim 7 wherein $R_6$ and $R_7$ are independently hydrogen.

10. O-malonyltryrosyl compounds of Formula (II) of claim 7 wherein $R_6$ and $R_7$ are independently tert-butyl or n-butyl; $R_8$ is hydrogen; $R_{10}$ is hydrogen; and $R_{10}$ is fluorenyl methoxy carbonyl, tert-butoxy carbonyl, or carbobenzoxy.

11. O-malonyltyrosyl compounds of Formula (II) of claim 7 wherein $R_6$ and $R_7$ are independently tert-butyl, n-butyl, or alkyl; $R_8$ is fluorine; $R_9$ is hydrogen; and $R_{10}$ is fluorenyl methoxy carbonyl, tert-butoxy carbonyl, or carbobenzoxy.

* * * * *

UNITED STATES PATENT AND TRADEMARK OFFICE
CERTIFICATE OF CORRECTION

PATENT NO. : 5,688,992
APPLICATION NO. : 08/414520
DATED : November 18, 1997
INVENTOR(S) : Terrence R. Burke, Jr. et al.

It is certified that error appears in the above-identified patent and that said Letters Patent is hereby corrected as shown below:

Cover, Title, and col. 1     change "O-MALONYLTRYROSYL COMPOUNDS, O-MALONYLTRYROSYL COMPOUND-CONTAINING PEPTIDES, AND USE THEREOF"
to -- O-MALONYLTYROSYL COMPOUNDS, O-MALONYLTYROSYL COMPOUND-CONTAINING PEPTIDES, AND USES THEREOF --

Cover, Other Publications,
Column 1, lines 8 & 9, change "(Difluoromethly)"
to -- (Difluoromethyl) --

Column 1, line 20, change "Inhibitos," to -- Inhibitors,--

P. 2, Column 2, line 6, change "Phosphotyrines" to -- Phosphotyrosine --

Abstract, line 2 change "O-malonyltryrosyl" to -- O-malonyltyrosyl --

Abstract, line 3 change "O-malonyltryrosyl" to -- O-malonyltyrosyl --

Abstract, line 4 change "O-malonyltryrosyl" to -- O-malonyltyrosyl --

Abstract, line 5 change "O-malonyltyrosyl malonyltyrosyl" to -- O-malonyltyrosyl --

Abstract, line 6 change "O-malonyltryrosyl" to -- O-malonyltyrosyl --

Abstract, line 9 change "O-malonyltryrosyl" to -- O-malonyltyrosyl --

Abstract, line 10 change "defivatization" to -- derivatization --

Abstract, line 12 change "O-malonyltryrosyl" to -- O-malonyltyrosyl --

Title page, item [54] Column 1, line 1, change "O-MALONYLTRYROSYL" to
-- O-MALONYLTYROSYL --

Column 1, line 2, change "O-MALONYLTRYROSYL" to
-- O-MALONYLTYROSYL --

UNITED STATES PATENT AND TRADEMARK OFFICE
CERTIFICATE OF CORRECTION

| | | |
|---|---|---|
| PATENT NO. | : 5,688,992 | |
| APPLICATION NO. | : 08/414520 | |
| DATED | : November 18, 1997 | |
| INVENTOR(S) | : Terrence R. Burke, Jr. et al. | |

It is certified that error appears in the above-identified patent and that said Letters Patent is hereby corrected as shown below:

Column 1, line 3, change "USE" to -- USES --

Column 1, line 8, change "O-malonyltryrosyl" to -- O-malonyltyrosyl --

Column 1, line 9, change "O-malonyltryrosyl" to -- O-malonyltyrosyl --

Column 1, line 12, change "O-malonyltryrosyl" to -- O-malonyltyrosyl --

Column 1, line 19, change "signai" to -- signal --

Column 1, line 59, change "kinare" to -- kinase --

Column 2, line 53, change "et at." to -- et al. --

Column 2, line 54, change "et at." to -- et al. --

Column 2, line 55, change "et at." to -- et al. --

Column 2, line 58, change "et at." to -- et al. --

Column 3, line 9, change "et at." to -- et al. --

Column 3, line 14, change "containing containing" to -- containing --

Column 3, line 24, change "et at." to -- et al. --

Column 3, line 45, change "signai" to -- signal --

Column 3, line 59, change "et at." to -- et al. --

Column 4, line 5, change "et at." to -- et al. --

Column 4, line 9, change "O-malonyltryrosyl" to -- O-malonyltyrosyl --

Column 4, line 10, change "O-malonyltryrosyl" to -- O-malonyltyrosyl --

Column 4, line 15, change "O-malonyltryrosyl" to -- O-malonyltyrosyl --

Column 4, line 22, change "O-malonyltryrosyl" to -- O-malonyltyrosyl --

Column 4, line 23, change "O-malonyltryrosyl" to -- O-malonyltyrosyl --

UNITED STATES PATENT AND TRADEMARK OFFICE
CERTIFICATE OF CORRECTION

PATENT NO.       : 5,688,992
APPLICATION NO.  : 08/414520
DATED            : November 18, 1997
INVENTOR(S)      : Terrence R. Burke, Jr. et al.

It is certified that error appears in the above-identified patent and that said Letters Patent is hereby corrected as shown below:

Column 4, line 31, change "O-malonyltryrosyl" to -- O-malonyltyrosyl --

Column 4, line 33, change "O-malonyltryrosyl" to -- O-malonyltyrosyl --

Column 4, line 34, change "O-malonyltryrosyl" to -- O-malonyltyrosyl --

Column 4, line 35, change "O-malonyltryrosyl" to -- O-malonyltyrosyl --

Column 4, line 36, change "O-malonyltryrosyl" to -- O-malonyltyrosyl --

Column 4, line 39, change "O-malonyltryrosyl" to -- O-malonyltyrosyl --

Column 4, line 43, change "O-malonyltryrosyl" to -- O-malonyltyrosyl --

Column 4, line 45, change "carboxylie" to -- carboxylic --

Column 4, line 61, change "kinare" to -- kinase --

Column 5, line 51, change "O-malonyltryrosyl" to -- O-malonyltyrosyl --

Column 5, line 59, change "O-malonyltryrosyl" to -- O-malonyltyrosyl --

Column 5, line 62, change "O-malonyltryrosyl" to -- O-malonyltyrosyl --

Column 5, line 66, change "O-malonyltryrosyl" to -- O-malonyltyrosyl --

Column 7, line 40, change "alaninc" to -- alanine --

Column 7, line 46, change "O-malonyltryrosyl" to -- O-malonyltyrosyl --

Column 7, line 57, change "aare" to -- are --

Column 8, line 13, change "glutamie" to -- glutamic --

Column 8, line 23, change "reeeptors" to -- receptors --

Column 8, line 28, change "C-terminai" to -- C-terminal --

Column 8, line 43, change "O-malonyltryrosyl" to -- O-malonyltyrosyl --

UNITED STATES PATENT AND TRADEMARK OFFICE
CERTIFICATE OF CORRECTION

PATENT NO. : 5,688,992
APPLICATION NO. : 08/414520
DATED : November 18, 1997
INVENTOR(S) : Terrence R. Burke, Jr. et al.

It is certified that error appears in the above-identified patent and that said Letters Patent is hereby corrected as shown below:

Column 8, line 44, change "O-malonyltryrosyl" to -- O-malonyltyrosyl --

Column 8, line 52, change "O-malonyltryrosyl" to -- O-malonyltyrosyl --

Column 9, line 30, change "O-malonyltryrosyl" to -- O-malonyltyrosyl --

Column 9, line 54, change "O-malonyltryrosyl" to -- O-malonyltyrosyl --

Column 10, line 39, change "O-malonyltryrosyl" to -- O-malonyltyrosyl --

Column 11, line 59, change "peprides" to -- peptides --

Column 11, line 65, change "hydrolyric" to -- hydrolytic --

Column 12, line 12, change "pepride" to -- peptide --

Column 12, line 12, change "Domehek" to -- Domchek --

Column 12, lines 49 & 50, change "(L)-$N^{60}$-fmoc-O'-[(O'',O''-(tertbutyl)malonyl]" to -- (L)-$N^{\alpha}$-fmoc-O'-[(O'',O''-(tertbutyl)malonyl] --

Column 13, line 42, change "SI-I2" to -- SH2 --

Column 14, line 9, change "O-malonyltryrosyl" to -- O-malonyltyrosyl --

Column 14, line 38, change "A:0.0555TFA in H2O," to -- A:0.05%TFA in $H_2O$,--

Column 14, line 64, change "$CH_2(CO_2-)$," to -- $CH_2(CO_2-)_2$ --

Column 16, line 9, change "et at." to -- et al. --

Column 18, line 50, change "Fmoc-OMT. OMT." to -- Fmoc-OMT. --

Column 19, line 19, change "Ac-Asn-[L-OMT]-Vai-Asn-Ile-Glu-amide" to -- Ac-Asn-[L-OMT]-Val-Asn-Ile-Glu-amide --

Column 19, line 33, change "rs." to -- vs. --

UNITED STATES PATENT AND TRADEMARK OFFICE
CERTIFICATE OF CORRECTION

PATENT NO. : 5,688,992
APPLICATION NO. : 08/414520
DATED : November 18, 1997
INVENTOR(S) : Terrence R. Burke, Jr. et al.

It is certified that error appears in the above-identified patent and that said Letters Patent is hereby corrected as shown below:

Column 20, line 5, change "GNGDpYMPMSPK" to -- GNGDpYMPMSP$\underline{K}$ --

Column 20, line 7, change "hmt" to -- hmT --

Column 20, line 8, change "KEPQpYEEIPIYL" to -- $\underline{K}$EPQpYEEIPIYL --

Column 20, line 11, change "DNDpYIIPLPDPK" to -- DNDpYIIPLPDP$\underline{K}$ --

Column 20, line 25, change "supematant" to -- supernatant --

Column 21, line 21, change "Ac-D-A-D-E-9L-FMOT)-L-amide" to
-- Ac-D-A-D-E-(L-FMOT)-L-amide --

Column 21, line 63, change "hydrolyrically" to -- hydrolytically --

Column 22, line 3, change "hydrolyrically" to -- hydrolytically --

Column 22, lines 21 & 22, change "L-Phenylaianine" to -- L-Phenylalanine --

Column 22, line 24, change "Anaiogues." to -- Analogues. --

Column 22, line 29, change "Chatterice," to -- Chatterjee --

Column 22, line 57, change "413423." to -- 413-423. --

Column 22, line 60, change "453481." to -- 453-481. --

Column 24, line 56, change "3-Kinase Kinase" to -- 3-Kinase --

Column 24, line 62, change "Lure," to -- Lum, --

Column 25, line 18, change "phosphate mimics." to -- mimics. --

Column 26, line 6, change "phosphates." to -- phosphatases. --

Column 26, line 23, change "Betchuck," to -- Berchuck, --

SEQUENCE LISTING, (2) INFORMATION FOR SEQ ID NO:5:
change "[I125]" to -- [I$^{125}$] --

UNITED STATES PATENT AND TRADEMARK OFFICE
CERTIFICATE OF CORRECTION

PATENT NO. : 5,688,992
APPLICATION NO. : 08/414520
DATED : November 18, 1997
INVENTOR(S) : Terrence R. Burke, Jr. et al.

It is certified that error appears in the above-identified patent and that said Letters Patent is hereby corrected as shown below:

SEQUENCE LISTING, (2) INFORMATION FOR SEQ ID NO:6:
change "[I125]" to -- $[I^{125}]$ --

SEQUENCE LISTING, (2) INFORMATION FOR SEQ ID NO:7:
change "[I125]" to -- $[I^{125}]$ --

Column 31, line 2, change "O-malonyltryrosyl" to -- O-malonyltyrosyl --

Column 31, line 26, change "O-malonyltryrosyl" to -- O-malonyltyrosyl --

Column 31, line 29, change "O-malonyltryrosyl" to -- O-malonyltyrosyl --

Column 31, line 31, change "O-malonyltryrosyl" to -- O-malonyltyrosyl --

Column 31, line 34, change "O-malonyltryrosyl" to -- O-malonyltyrosyl --

Column 32, line 1, change "O-malonyltryrosyl" to -- O-malonyltyrosyl --

Column 32, line 25, change "O-malonyltryrosyl" to -- O-malonyltyrosyl --

Column 32, line 28, change "O-malonyltryrosyl" to -- O-malonyltyrosyl --

Column 32, line 30, change "O-malonyltryrosyl" to -- O-malonyltyrosyl --

Column 32, line 32, change "$R_{10}$ is hydrogen;" to -- $R_9$ is hydrogen; --

Signed and Sealed this

Twenty-sixth Day of June, 2007

JON W. DUDAS
*Director of the United States Patent and Trademark Office*